US012290235B2

(12) United States Patent
Street et al.

(10) Patent No.: US 12,290,235 B2
(45) Date of Patent: *May 6, 2025

(54) WIRELESS LAPAROSCOPIC DEVICE WITH GIMBALLED CAMERA

(71) Applicant: Raytrx, LLC, Tulsa, OK (US)

(72) Inventors: David Street, Medford, OR (US);
Michael H. Freeman, Tulsa, OK (US);
Jordan Boss, Tulsa, OK (US);
Mitchael C. Freeman, Tulsa, OK (US);
Steven Yeager, Tulsa, OK (US);
Victoria McArtor, Tulsa, OK (US);
Brian Santee, Tulsa, OK (US);
Montgomery H. F. Freeman, Tulsa, OK (US)

( * ) Notice: Subject to any disclaimer, the term of this patent is extended or adjusted under 35 U.S.C. 154(b) by 71 days.

This patent is subject to a terminal disclaimer.

(21) Appl. No.: 17/944,995

(22) Filed: Sep. 14, 2022

(65) Prior Publication Data

US 2023/0172432 A1 Jun. 8, 2023

Related U.S. Application Data

(63) Continuation of application No. 17/473,689, filed on Sep. 13, 2021, now Pat. No. 11,478,140.

(60) Provisional application No. 63/078,517, filed on Sep. 15, 2020.

(51) Int. Cl.
*A61B 1/00* (2006.01)
*A61B 1/05* (2006.01)
*A61B 1/06* (2006.01)
*A61B 1/313* (2006.01)

(52) U.S. Cl.
CPC ...... *A61B 1/00098* (2013.01); *A61B 1/00006* (2013.01); *A61B 1/00018* (2013.01); *A61B 1/00066* (2013.01); *A61B 1/00087* (2013.01); *A61B 1/00096* (2013.01); *A61B 1/00147* (2013.01); *A61B 1/05* (2013.01); *A61B 1/0676* (2013.01); *A61B 1/0684* (2013.01); *A61B 1/3132* (2013.01)

(58) Field of Classification Search
CPC ............ A61B 1/00006; A61B 1/00018; A61B 1/00066; A61B 1/00087; A61B 1/00096; A61B 1/0676; A61B 1/0684; A61B 1/3132
See application file for complete search history.

(56) References Cited

U.S. PATENT DOCUMENTS

| 6,371,964 | B1 * | 4/2002 | Vargas | A61B 17/32053 |
| | | | | 606/153 |
| 6,817,974 | B2 | 11/2004 | Cooper et al. | |
| 11,478,140 | B1 * | 10/2022 | Street | A61B 1/3132 |
| 2002/0043266 | A1 | 4/2002 | Toti et al. | |

(Continued)

*Primary Examiner* — Timothy J Neal

(57) ABSTRACT

A laparoscopic imaging apparatus is described herein. The laparoscopic imaging apparatus includes a shaft having a proximal end opposite a distal end, wherein the proximal end is configured for attachment to an actuator, and the distal end is configured for attachment of a laparoscopic tool and for insertion into patient anatomy. The laparoscopic tool pivots on a first gimbal apparatus that is actuable from the actuator at the proximal end of the shaft, to rotate the laparoscopic tool about a longitudinal axis of the shaft and, further, to rotate the laparoscopic tool about at least a second axis that is orthogonal to the longitudinal axis.

18 Claims, 16 Drawing Sheets

(56) References Cited

U.S. PATENT DOCUMENTS

| | | | |
|---|---|---|---|
| 2005/0288622 A1* | 12/2005 | Albrecht | A61M 13/003 604/23 |
| 2016/0338571 A1 | 11/2016 | Haraguchi | |
| 2019/0183641 A1 | 6/2019 | Ganesan et al. | |
| 2021/0330174 A1 | 10/2021 | Yang et al. | |

* cited by examiner

210

212

212

214

WIRELESS LAPAROSCOPIC DEVICE WITH GIMBALLED CAMERA

CROSS REFERENCE TO RELATED APPLICATIONS

This is a continuation of U.S. patent application Ser. No. 17/473,689, filed Sep. 13, 2021, which claims the benefit of U.S. Provisional Application Ser. No. 63/078,517, filed Sep. 15, 2020, the disclosures of which are hereby incorporated by reference in their entirety.

FIELD OF THE INVENTION

The disclosure relates generally to camera-aided surgical instruments, and more particularly to devices adapted to be used during laparoscopic surgery or endoscopic inspection or surgery. The disclosure also covers a means and method to virtually map the instruments and laparoscope as they are being used, with a virtual guidance system overlay visible through an AR/XR headset.

COPYRIGHT NOTICE

A portion of this disclosure contains material that is subject to copyright protection. The copyright owner has no objection to the facsimile reproduction by anyone of this patent document as it appears in the U.S. Patent and Trademark Office, patent file or records, but reserves all copyrights whatsoever in the subject matter presented herein.

BACKGROUND

In traditional "open" surgery the surgeon uses a single incision to enter the body. Open surgeries typically require a large incision, which requires time to heal and most often leaves large scars. On the other hand, surgical scopes are among the oldest forms of medical instrumentation, with some of the earliest examples on record dating to 70 AD. Initially comprised of simple hollow tubes, over time these rudimentary telescopes were adapted to include magnifying lenses, then illumination, eventually developing into the digital surgical scopes used today. However, present day laparoscopes and endoscopes have major drawbacks which are improved by the teaching of this instant patent.

Laparoscopic or endoscopic surgeries have gained popularity in the last decade and are deemed to be minimally invasive for the patient providing less tissue damage, faster recovery, and relatively small scars. In laparoscopic surgery a surgeon uses several small keyhole incisions called "ports". At each port, a trochar (a narrow tubular instrument capable of piercing the skin and tissue) is inserted. Some auxiliary ports are used to insert specialized instruments to clamp, excise, resect, cut, cauterize, or sew tissue. Prior to the surgery, the abdomen or pelvis is filled with carbon dioxide gas to inflate the area, so as to provide a working and viewing space for the surgeon. Typical surgeries using the laparoscopic instruments are bowel resection, gall bladder removal, and spleen removal.

Currently in the art, a typical laparoscopic has a fixed camera mounted at the top of the tubular device which provides the surgeon with a small area of visualization during the surgery. Commonly, there is a "straight" laparoscopic device, and 30 degree (curved) laparoscopic device and a 45 degree (more severe curve) laparoscopic device. These are interchanged throughout a surgery according to where the surgeon needs to look. However, a constant drawback is that once one laparoscopic is withdrawn and another one inserted (to see a different angle) there is pressure on the tissue with each entry and exit causing damage. Further in a typical configuration, the camera is in the handle of the laparoscopic device with a light tube that permits the camera to see approximately 35 to 45 degrees field-of-view (FOV), Thus, there is a need in the art for just one laparoscopic instrument which accomplishes all these tasks without having to be extracted and reinserted, and such instrument with a much wider field-of-view.

On an endoscope, the camera may be at the tip of the insertion tube. In either case, the camera feed is through a tethered cord back to a monitor which the provides the surgeon internal views during the surgery. Endoscopic surgery is performed using, as the visualization device, a flexible tube with a camera and light at the tip. Before such devices were digitized, they operated as miniature telescopes, with limited FOV, as noted above.

However, the surgeons' view from any one camera is limited by the fact that the camera is at the top of the trochar and looks down the long tube, thus providing a limited field-of-view (FOV), often not more than 45 degrees FOV. This necessitates the surgeon manipulating the laparoscope within the port to search for a target region or moving from port to port to detect target tissue or organs due to the limited FOV. In some cases, more than one laparoscope is used to attempt to view more of the internal space and organs. The use of a camera allows the procedure to be viewed by one or more surgical personnel simultaneously and allows the video feed to be recorded.

Endoscopy is commonly used to inspect the throat, or for inspection and surgery on the colon, like laparoscopic surgeries, endoscopic surgeries are procedures accomplished without making major incisions, allowing for easier recovery time and less pain and discomfort. For the purposes of the present disclosure, both laparoscopes and endoscopes are collectively called "scopes".

In surgical practice, the constant maneuvering of the scopes, combined with the limited FOV, can extend surgical duration, and increase the chance for unintended tissue damage, generating operative concerns and longer patient recoveries. Both laparoscopic and endoscopic devices have cameras either at the top, placed somewhere in the length of the tube chamber or, less commonly, at the tip of the device. All of these devices suffer from a limited FOV and are tethered to cables used for data flow and light.

Additionally, because of the limited FOV, existing laparoscopic technologies require the surgeon, assistant, or tech to understand and retain a mental image of the hidden organs and anatomical features of the patient as the laparoscopic device is moved around the tissue and organs. The narrow telescopic view of an earlier laparoscopic device with a camera mounted at the proximate end cannot capture the full image of the target; in effect, the camera can be considered as "looking down a barrel". In an attempt to compensate for this problem, many existing telescopic laparoscope devices, whether flexible or rigid, provide an oblique view, which is not coincident with the main axis of the camera, and is therefore an inferior image or video.

Moreover, upon insertion, the lens at the distal end of the camera tube of a typical laparoscopic device often fogs, extending surgery time and degrading the efficiency of the operation. Moreover, if there is significant inflammation, or if the surgeon encounters tissue or organ obstructions that prevent a clear view of the target, the surgeon often needs to make a larger incision in order to complete the operation safely or needs to move the one or more laparoscopes, which requires more "ports" to be inserted into the patient. Sometimes an incision large enough for a hand to be inserted is then required, which is called "hand" assisted laparoscopic surgery.

Thus, the constraints of narrow FOV and limited ability for camera movement without concomitant displacement of organs and tissue, present significant difficulties in surgical science. Some advanced laparoscopic camera techniques address camera problems by connecting an array of cameras in one or more ports, deployed to provide a stitched video in order to expand the FOV, potentially with smaller blind spots. However, the effort required to insert multiple cameras from multiple ports adds significant time to surgery, with additional incisions, and can introduce burdensome camera cords extending over the operating table, over the patient, and all over the operating room (OR). Often, these multi-camera techniques are rife with technical difficulties and can even mandate presence of an electronics expert to ensure the correct operation of the camera array. Other manufacturers have tried to improve FOV by placing either "zero" (cameras aimed straight ahead) camera diagonal tips, such as a "30 degree" or "40 degree" tip with the cameras angled to a specific set side-directionality. Another has offered "pop-up" mid-tube up cameras; however, these cameras, especially the "pop-up" camera, are often obstructed by tissue or organs, and thus are not a significant improvement over the current medical standards. The pop-up camera also has the additional defect of "catching" on an organ, tissue, or veins, causing damage to the patient.

Further, while laparoscopic surgery is typically less invasive and easier to recover from than "open" surgery, during the surgery, a surgeon must work, mostly in the blind because of the tight densely organ populated area, and surgeons struggle with exactly where they are inside the complex environment of a body cavity during laparoscopic surgery. Conducting laparoscopic surgery therefore takes time and practice to get it right and have the right result for the patient.

Thus, there is a need in the art for a positioning and guidance system, not only for the laparoscopes, but for the myriad of other tools which must be inserted into the body though the trochars.

While others have attempted to develop a "smart trocar" system that knows when an instrument is inserted and removed from a trocar and how long it was inserted, this information fails to provide the surgeon with the real-time information nor provides a virtual map of where all the instruments and laparoscopes are while the surgery is still being conducted. The previous solution was based on a trocar mounted camera combined with a computer vision algorithm. The instant disclosure provides a 3D visualization method for 3D mapping the laparoscopes and tools as they are being used during surgery. This accomplishes three important laparoscopic surgery needs: (i) training and practice for beginning laparoscopic surgeons; (ii) a mapping and tracking system involving all the tools and instruments inside the patient's body that can show a surgeon where it is safe to move the tools and prevent the surgeon from having one tool or instrument conflict with another or an internal structure, and (iii) promote the art of three dimensional imaging for surgery applications, which more accurately portrays the body than when viewed in 2D.

There is thus considerable need for improvement to conventional laparoscopic devices and technique.

SUMMARY OF THE INVENTION

It is an object of the present disclosure to advance the art of laparoscopic surgery and to address problems such as those previously noted in the background section.

An advantage of the Scopetrx™ laparoscope of the present disclosure relates to range of movement: the camera can swivel by 360 degrees on the 'barrel' which is the x axis and by approximately 270 degrees on the y axis represented by the internal gimbal system. Features of the camera, sensors and lens, and camera placement at the forefront of manipulability in what the surgeon can see internally, a distinct advantage over conventional laparoscopic or endoscopic devices which must be removed and replaced with another angle. Moreover, using the instrument with the optional flex-cable component of the camera barrel adds another measure of flexibility of movement of the camera. As a distinct benefit of this system, fewer incisions are needed during surgery, such as can be otherwise required for visibility of the surgical site. In addition, one version of the embodiment is contained within an 0.08 mm canulae so that a suture is not needed when the Swivel Laparoscopic device is removed.

The increased FOV and manipulation of the camera provide an improved picture of the target region. With the camera sub-system at the end of the tube, the instrument can capture and present the largest FOV at the target site, with as much as 90¬110 degrees FOV, as opposed to configurations with camera systems at the top of the laparoscope or in the mid-section of the barrel.

A more particular benefit of the Scopetrx™ laparoscope (Ocutrx, Orange County, CA) of the present disclosure relates to reducing the number of tools used in surgery, since the Applicant's instrument is both an obturator and camera system housed in the same trochar. In addition, the device's tubes are detachable for sanitizing and are made of a biocompatible material which can be sterilized.

Another unique feature of the Scopetrx instrument of the present disclosure is the fact that the surgeon can adjust the angle of the camera units at the end of the sub-tube as a unit, with the same hand that is used for opening and closing the trochar blades. Hence, the surgeon's other hand is free to operate a second laparoscopic instrument.

Yet another advantage of the Scopetrx instrument is the presence of a wireless mechanism in order to minimize or eliminate troublesome cords extending from the laparoscope device. This feature not only removes the cords from the operating table and the operating room, but permits the surgeon to also wear an un-tethered augmented reality headset with a compatible wireless receiver which presents the surgery view, so that there can be a seamless transfer of video and data to the surgeon from the device. This can be a significant advantage to the ergonomics of the surgery for the surgeon. Especially beneficial to the surgeon, because the Scopetrx laparoscope is wireless it can send wireless video information to a receiving AR/XR headset, like the ORLenz™ Surgery headset or to a monitor like the StereoLenz 3D autostereoscopic 8K monitor, which does not require 3D glasses to see an image in 3D, due to the lenticular lenses when combined with the software shaders extant in the StereoLenz.

It is also advantageous in that the surgeon while wearing an AR/SXR headset can see both the inside and outside of the patient simultaneously, so that all concerns of a surgery are before the surgeon's eyes. Another advantage is that data about the patient's conditions, like patient vitals can also be projected onto the surgeon's augmented reality or virtual reality headset. Likewise, tool information, such as the temperature of a cauterizing tip for example, can be shown on the headset, so that useful information concerning the patient is immediately available to the surgeon.

Another advantage of the Scopetrx laparoscopy is that is that it can have both a rechargeable battery and an embedded battery. The embedded battery within the battery circuitry system maintains power to the camera and controls during a battery exchange procedure, so that a "hot-swap" can be accomplished. Hot-swap, as used herein means that operating power is sustained for a limited time so that the tool does not power-off during a battery swap.

Still another advantage of the Scopetrx laparoscopic device is the presence of a locking mechanism to fix the angle of the camera so as to stabilize and maintain a certain viewing area on a target.

Yet another advantage of the Scopetrx laparoscopic device of the present disclosure is the inclusion of a depth gauge housed in the device with a digital instrumentation on the handle and as data with the video feed, which helps the surgeon determine the depth of the cut or intrusion being made.

A particular advantage of a wireless system is that the surgeon does not have to deal with cords while holding and working the device, permitting easier insertion, use, and angle manipulation. Also, the added benefit of wireless signal communication is that none of the surgery team has to connect, account for, or deal with the myriad of cables which typically exist with standard scopes both all over the operating table and operating room.

The wireless data and video can be sent to any device having a compatible receiving unit, including a wearable augmented reality (AR) display. This can include, but would not be limited to, sending the image content and related information to the ORLenz Augmented Reality Surgery Headset. In this fashion, the surgeon can visualize the internal operation and location of the Scopetrx laparoscope while also easily observing external aspects of the patient during surgery. This information can be displayed to the practitioner wearing an AR/XR headset, such as for display along the periphery of the field, such as along the bottom, side, or top, depending on viewer preference.

In addition, with visualization connection from the Scopetrx laparoscope to a surgical support system, such as but not limited to the ORLenz system from Ocutrx, Orange County, CA, virtual text, and data can be combined with the surgery video feed from other sources, like a blood pressure system, a pulse oxygenation system or heart-rate/blood pressure systems. For instance, a visualization system, such as but not limited to the MedTiles™ visual subsystem for display in an AR/XR headset, can provide a presentation overlay of vital information (text and graphs) in virtual display either overlaid onto, or in addition to, the operating view. These can be presented using Six Degrees of Freedom (6DoF) and "posing" techniques onto the FOV of the headset lens. The MedTiles visualization system is a product of Ocutrx, Orange County, CA and provides display features similar to windows or chyron generated and virtually presented.

Moreover, the Scopetrx laparoscope can be used with a Surgery Visualization Theatre, such as but not limited to the OR-Bot™ visualization system, which can receive the signal and display the video and data on a multitude of visualization platforms, including but not limited to the ORLenz AR headset, the StereoLenz™ 8K 3D Autostereoscopic "glasses-free" monitor, or the MiniLenz™ microscope-type virtual reality viewing. The advantage of this setup is that, rather than being sent to one specific wireless receiving monitor, the OR-Bot system can take the signal and render image content over a number of display media, in a connected telemedicine method, including displaying the video remotely in the instance of expert-assisted surgery, where a remote surgeon, team, or other viewer can visualize the internals captured by the cameras and assist the surgeon physically onsite with information, advice, instruction, or caution. All of these visualization methods provide improved ergonomics over instruments currently available to an endoscopic or laparoscopic surgeon.

Also, the OR-Bot system or the ORLenz system can be used with 5G communication to visualize areas obscured by surgical instruments in laparoscopic procedures, making the tools appear invisible according to the methods described herein.

With the Scopetrx laparoscope, video feed intelligence in the combined software permits shaders and other image processing software utilities to be used which can generate, for the surgery team and others, computer-generated imagery of the surgery feed which can produce a range of enhancing or monitoring effects. Beyond just simple lighting models, more complex uses of shaders on the video feed include altering the hue, saturation, brightness, or contrast of an image, producing blur, light bloom, volumetric lighting, grid or x, y, z mapping for depth effects, bokeh, depth-of-field, cell shading, pixel manipulation, posterization, bump and displacement mapping, grey-scaling, distortion, chroma keying, edge detection, fiduciary marking, motion detection, and a wide range of other techniques. While many of the advantages mentioned above are clear, in the instance of motion detection, this can be used with advanced signal processing in the Scopetrx laparoscope to record if a suture is holding or alert if the tissue is moving or tearing.

Another advantage of sending the wireless video and data to a surgical support system, including but not limited to an OR-Bot system, is that it can then be recorded, preserved, analyzed, and used in other surgeries to point out important information like the correct choosing of a critical surgery option choice. In this fashion, the video and data can be processed using Artificial Intelligence and machine learning algorithms to assess information gleaned through the surgery.

In addition, the surgeon, while using any of the visualization methods of the OR-Bot 3D Surgery Visualization Theatre or other suitable visualization system, can see other pertinent information overlaid over the actual tissue or organs seen from the video feed. For instance, while using a wearable display, such as, but not limited to the ORLenz Augmented Reality Surgery headset, the surgeon can also have patient vital statistics either superimposed over the surgery video feed or appearing as if in space, without blocking the surgery video feed.

To further facilitate use of the apparatus of the present disclosure, a number of different output modes are provided for sending and transmitting information from the imaging instruments to the operating room staff.

According to an embodiment of the present disclosure, there is provided a laparoscopic imaging apparatus comprising a shaft having a proximal end opposite a distal end, wherein the proximal end is configured for attachment to an actuator, wherein a longitudinal axis extends through the shaft, between the proximal and distal ends, wherein the distal end is configured for insertion into patient anatomy and for attachment of one or more laparoscopic tools, wherein at least a first laparoscopic tool at the distal end pivots on a first gimbal apparatus that is actuable, from the actuator at the proximal end of the shaft, to rotate the at least the first laparoscopic tool about the longitudinal axis of the shaft and, further, to rotate the at least the first laparoscopic tool about at least a second axis, orthogonal to the longitudinal axis.

It is to be understood that both the foregoing general description and the following detailed description are merely exemplary and are intended to provide an overview or framework to understand the nature and character of the claims.

The accompanying drawings are included to provide a further understanding and are incorporated in and constitute a part of this specification. The drawings illustrate one or more embodiment(s), and together with the description serve to explain principles and operation of the various embodiments.

With the foregoing and other advantages and features of the disclosure that will become hereinafter apparent, the nature of the Applicant's solution may be more clearly understood by reference to the following detailed description, the appended claims and to the several views illustrated in the drawings.

BRIEF DESCRIPTION OF THE DRAWINGS

Other advantages of the present disclosure will be readily appreciated as the same becomes better understood by reference to the following detailed description, when considered in connection with the accompanying drawings.

DETAILED DESCRIPTION

Figure 1:
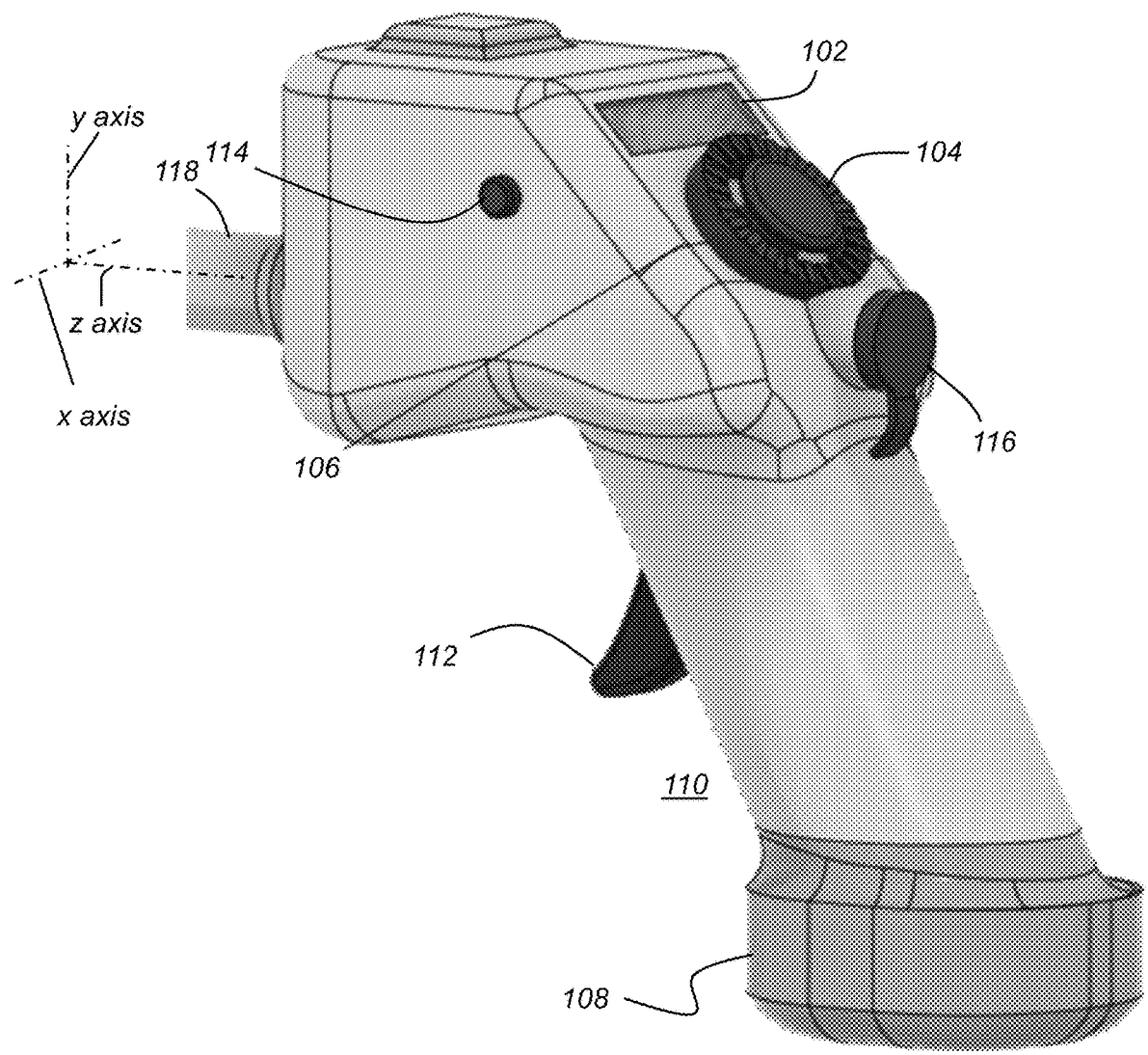
FIG. 1 is a perspective view showing the swivel-camera laparoscopic tool viewed from the left side of the handle according to an embodiment of the present disclosure.
Figure 2:
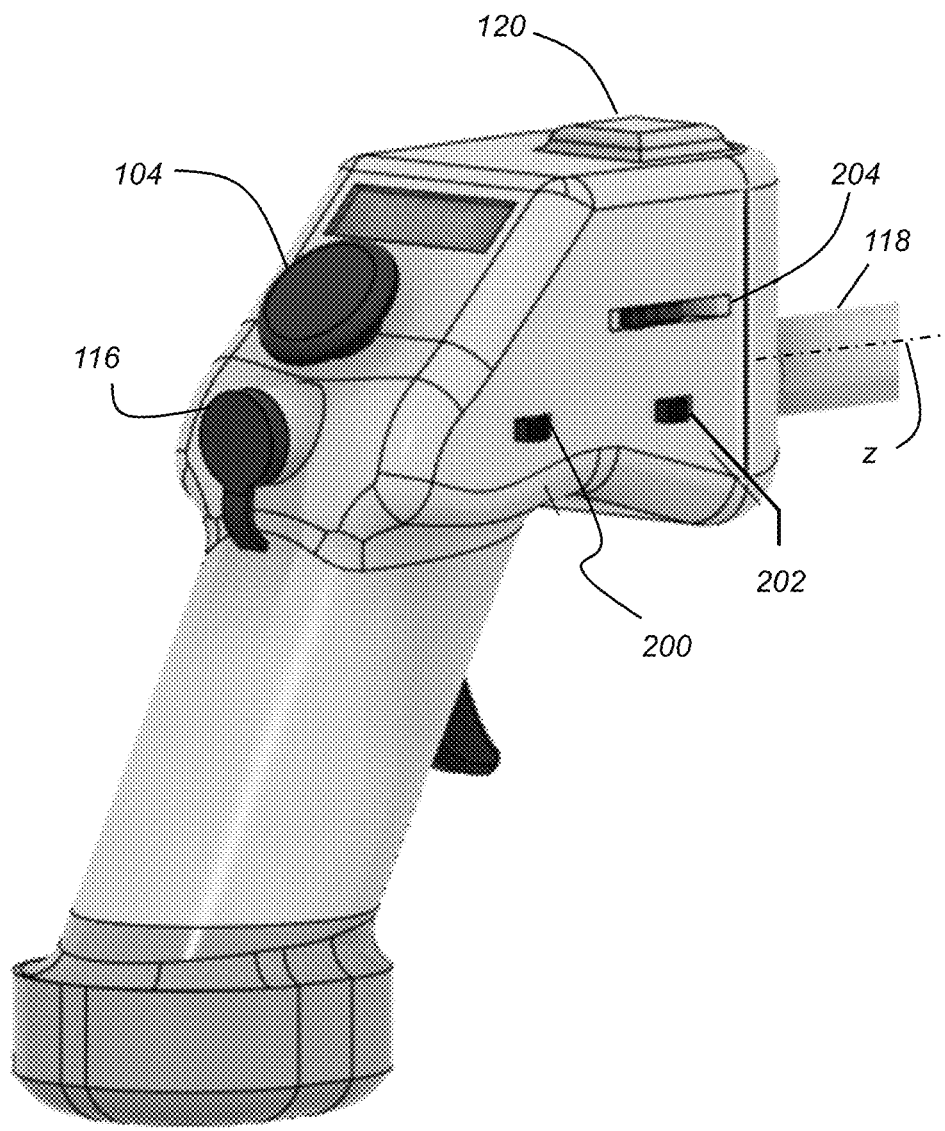
FIG. 2 shows the swivel-camera laparoscopic tool viewed from the right side of the handle according to an embodiment of the present disclosure.

Figures shown and described herein are provided in order to illustrate key principles of operation and fabrication for an optical apparatus according to various embodiments. Figures are not drawn with intent to show actual size or scale. Some exaggeration may be necessary in order to emphasize basic structural relationships or principles of operation.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification. It will be apparent to one having ordinary skill in the art that the specific detail need not be employed to practice according to the present disclosure. In other instances, well-known materials or methods have not been described in detail in order to avoid obscuring the present disclosure.

The devices and methods discussed herein are merely illustrative of specific manners in which to make and use this invention and are not to be interpreted as limiting in scope. While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

As used herein, "Augmented and Extended Reality" (AR/XR) is defined herein in its common scientific use, which may include an interactive experience typically in a see-through headset with lenses of a real-world environment where the objects that reside in the real world are enhanced by computer-generated perceptual images and information, sometimes across multiple sensory modalities, including visual, auditory, haptic technologies, somatosensory, and/or olfactory. As used herein an AR/XR headset may also be a Virtual Reality device or headset.

"Extended Reality" is defined in its common scientific use, which is typically an umbrella term encapsulating augmented reality (AR) and/or virtual reality (VR) and/or mixed reality (MR) and/or real reality (RR) and everything in between. It may also include combined environments and human-machine interactions generated by computer technology such as 6DoF and SLAM, and artificial intelligence (AI), including machine learning (ML), where the 'X' represents a variable for any current or future spatial computing technologies, including digital content of any sort; for instance, in the medical field, a 3D MRI or CT scan images or data visualizations, like patient vitals, superimposed or overlaid on an AR/XR headset in one of the several methods outlined herein.

"Artificial Intelligence" (AI), sometimes called "Machine Learning" (ML), is used herein in its common scientific meaning, including referring to the simulation of human intelligence in machines that are programmed to think like humans and mimic their actions and decisions. The term may also be applied to an augmented reality headset that exhibits traits associated with a human mind, such as learning and/or problem-solving. AI may enable AR to interact with the physical environment in a multidimensional way. For instance, AI may permit object recognition and tracking, gestural input, eye-tracking, and voice command recognition to combine to let the user manipulate 2D and 3D objects in virtual space with the user's hands, eyes, and/or words.

The term "image(s)" or "virtual image(s) or "imaging" or "virtual objects" or "AR/XR imaging" is defined for the purpose of this patent as visualization of either 2D images or video or 3D images or video. The definition also includes the concept that one or more 2D images can be viewed in stereoscopy to create one or more virtual 3D perspectives. Further included in the "image(s)" definition, herein, is the idea that AR/XR 3D models may be viewed as a single or series of 2D images, as in a still picture or video, or a single or series of stereoscopic 3D images, as in a 3D images or video. The 3D effect may be created in the AR/XR headset by using an offset paired perspective of a 3D model. In addition, 3D models in AR/XR can be viewed from different perspectives by the user or multiple users can view the same image from multiple perspectives.

The term "wireless" as used herein means the electromagnetic transfer of information between two or more points which are not connected by an electrical conductor, or a communication by technologies, such as light, magnetic, or electric fields, or the use of sound. The term "wired" communication as used herein includes all methods of wireline communication including, but not limited to, directly connected devices, telephone networks, ethernet connections, cable networks, internet access, fiber-optic communications, and waveguide (electromagnetism) connections.

"Object Recognition" (OR) or "Object Identification" (OI) is used herein in its common scientific meaning, including a computer vision technique for identifying objects in images or videos. Object recognition may be a key output of deep learning and AI algorithms. When humans look at a photograph or watch a video, we can readily spot people, objects, scenes, and visual details. OR/OI does this from visual analysis based on a neural network algorithms reconciliation with pre-existing information.

Simultaneous Localization and Mapping" (SLAM) is used herein in its common scientific meaning, including a technology that understands the physical world through a 3D grid of feature points. SLAM maps what the camera and sensors see in three dimensions with correct spatial information and distancing. This may make it possible for AR/XR applications to recognize RR 3D objects and scenes, as well as to instantly track motion in the RR, and to overlay digital interactive augmentations. SLAM incorporates the application of sensors sensing dept, time-of-flight, and creating a 3D grid. SLAM also incorporates infrared sensing and measurements.

The term "computer vision" is an interdisciplinary scientific field that deals with how computers can gain higher-level understanding from digital images or videos, beyond what a human can recognize or understand. The Scopetrx programs tasks and includes methods for acquiring, processing, analyzing, and understanding digital images or video, and extraction of high-dimensional data in order to produce pixel, dexel (sub-pixel), texel, voxel (a volumetric representation of a pixel rather than a picture, which may consist of a single piece of data, such as an opacity, or multiple pieces of data, such as a color in addition to opacity), numerical, or symbolic information, which can be used as higher analysis of the real-world information for specific characteristics. As used in the laparoscopic instrument, the software, program, and model controller may then take this information and apply it to an algorithmic logic to achieve an instantaneous new visual understanding of the image or video presented to the viewer, often one which the human eye could not detect and cannot distinguish. The enhanced image data from the laparoscopic instrument's processing may take many forms, such as video sequencing, views from multiple angles or cameras, or multi-dimensional data from a 3D imaging.

Singular terms such as "camera," "battery," or "wireless module" in the present disclosure are illustrative and non-limiting, and embodiments of the present disclosure can also include a plurality of these and other components.

Reference throughout this specification to "one embodiment," "an embodiment," "one example," or "an example" means that a particular feature, structure, or characteristic described in connection with the embodiment or example is included in at least one embodiment of the present disclosure. Thus, appearances of the phrases "in one embodiment," "in an embodiment," "one example," or "an example" in various places throughout this specification are not necessarily all referring to the same embodiment or example. Furthermore, the particular features, structures, or characteristics may be combined in any suitable combinations and/or sub-combinations in one or more embodiments or examples.

The term "laparoscopic tool" can refer to a camera, an illumination apparatus, or other type of tool for cutting, separating, measuring, sampling, extracting, collecting, or providing a material or fluid, for example. The term "laparoscopic tool" can also refer to any endoscopic tool such as an insufflator, grasping forceps, bipolar forceps, scissors, biopsy spoon, needle driver, torcher, and cryosurgical tool, for example or to some other type of laparoscopic instrument.

Several (or different) elements discussed herein and/or claimed are described as being "in communication with," "integrated," or "configured to be in communication with" or a "system" or "subsystem" thereof. This terminology is intended to be non-limiting and, where appropriate, be interpreted to include, without limitation, wired and wireless communication using any one or a plurality of a suitable protocols, as well as communication methods that are maintained continuously, active on a periodic basis, and/or initiated or active on an as-needed basis.

Where they are used, the terms "first", "second", and so on, do not necessarily denote any ordinal, sequential, or priority relation, but are simply used as descriptive terms that help to distinguish one element or set of elements from another in a clear manner, unless specified otherwise.

In the context of the present disclosure, the term "coupled" is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components.

In order to surmount viewing limitations of conventional laparoscope devices as described previously, the Applicant's solution disposes a camera at the distal tip of the insertion shaft in a gimballed configuration. As is familiar to those skilled in mechanics, a gimbal device provides two mutually perpendicular and intersecting axes of rotation, allowing a range of angular movement in two directions for a device that is mounted thereon. With reference to the axis designations shown in FIG. 1, the camera, thus supported, is able to rotate about the z axis, or more properly, about a rotation axis that is parallel to the z axis. The z axis itself corresponds to the longitudinal center axis of shaft 118. The camera is also capable of 270 degrees angular motion about the y axis, which is orthogonal to the rotation axis. Therefore, the system of the present disclosure can provide a larger FOV (field of view) than is provided by conventional systems. This gimballed support frees up a surgical port and eliminates at least some amount of physical maneuvering of the entire laparoscopic tube, which can disrupt organs and tissue, because the camera is able to turn and twist independently, to permit additional viewing areas of the target area. As a consequence, for example, the Applicants' system can provide larger extent of intra-abdominal visualization which may help to speed surgery and can provide improved efficiency during the operation, which can help to reduce the overall cost of the operation.

In the instant device, some of the features are operated by mechanical configuration under manual control. In an alternate embodiment, these features can be activated and operated electronically including the use of electronically activated motors and servo controllers. An embedded computer and a non-transitory model view controller (MVC) may synchronize the subsystems and may control all input and output according to the software programs and automatic or manual input control.

Handle 110 Subsystem

According to an embodiment of the present disclosure, the laparoscope device comprises a handle subsystem with one or more batteries, controllers, circuit boards and wireless modules, camera modules (sensor, camera, and circuit/power board and lens), and antennas for sending and receiving data and video. Handle 110 may also house and control all the subsystems related to laparoscope manipulation.

FIGS. 1 through 5 show aspects of a handle and housing subsystem that incorporates various electronic controllers and motors, combined with one or more circuit boards and a method for a digital readout of information. Affixed to the handle 110 is a tubular housing containing one or more internal barrels, upon which can be mounted cameras or other tools, or tool channels and supporting devices.

FIG. 1 shows a handle 110 of a swivel-camera laparoscopic apparatus, viewed from the left side of the handle according to an embodiment, wherein handle 110 has ergonomic design and is designed for operator grip, comfort, and control. An optional control roll wheel 106 is disposed on the side of handle 110. Roll wheel 106 can be used to roll the installed tool 360 degrees about the z-axis. A safety trigger 112 provides a mechanical interlock for roll wheel 106 rotation, locked in position unless trigger 112 is actuated.

A shaft 118 extends from handle 110 at its proximal end and provides an external shell or housing for tubing that extends within the shaft 118 and can be coupled to various tools that are then inserted into the patient during the surgical procedure. The center axis of shaft 118 corresponds to the longitudinal z-axis extending outward from handle 110, as shown in FIG. 1. The distal end of shaft 118 is configured to mechanically support one or more laparoscopic tools that are controlled from handle 110; including camera and other laparoscopic tools. According to an embodiment, an 8 mm diameter shaft 118 is provided for minimal intrusion. A 12 mm diameter shaft is provided for support of an additional tool, thus allowing two tools to be extended and manipulated from handle 110.

A digital display 102 provides a readout panel for display of information on instrument configuration and positioning. Display 102 can indicate tool extension distance, such as in Imperial or SI Units. When in piercing tool mode, the display can show the percentage for tool opening, for example. Units can be selected using a units button 114 as a type of control toggle. Tool values displayed can be switched using a tool selection toggle switch 200. Tool selection toggle switch 200 can be used to toggle between options that include selection of camera system, piercing tool, or bottom tool, for example.

A joy stick control 104 can be used to control movement of the selected coupled tool up to 270 degrees about the y-axis. Control 104 can be enabled by actuating safety trigger 112. A tool loader 116 allows tools to be attached onto or removed from the distal end of shaft 118, as needed.

Figure 3:
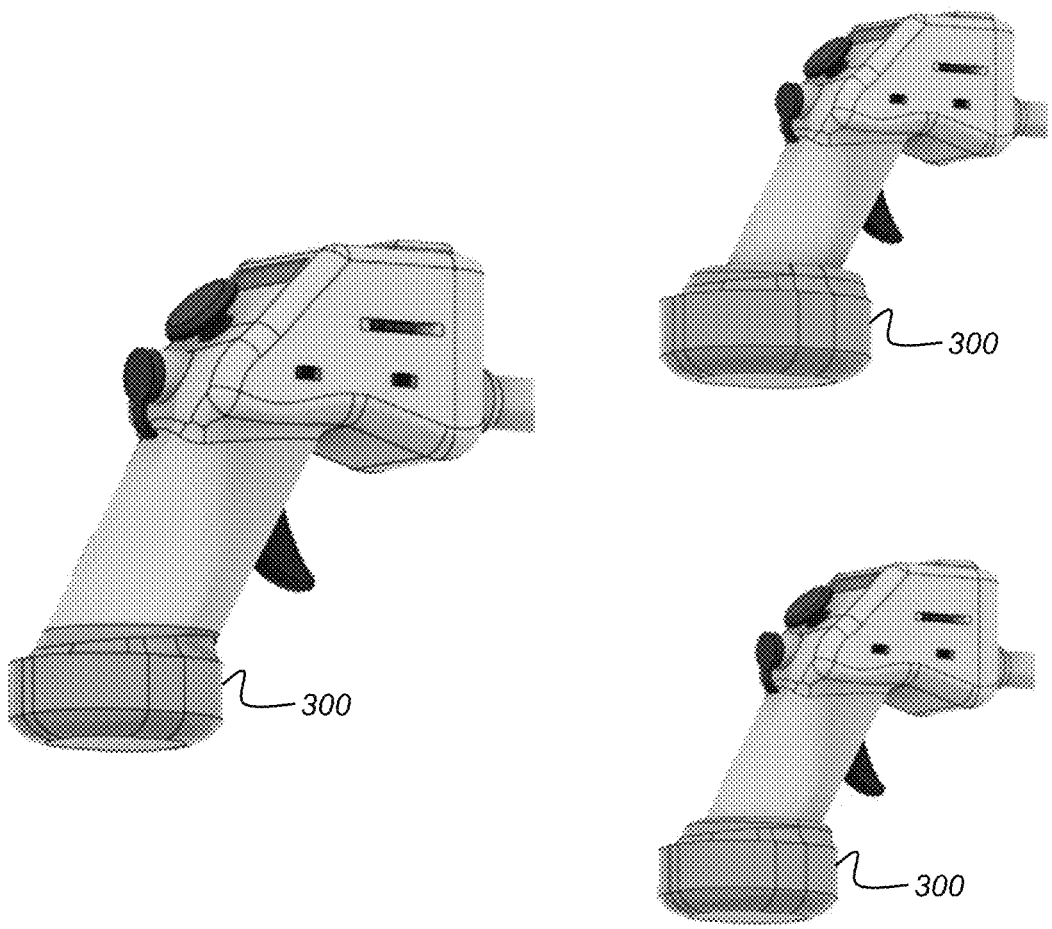
FIG. 3 shows three battery pack configurations.

A rechargeable battery 108 can be housed within handle 110. According to an embodiment of the present disclosure, a lithium-ion battery is used. As shown in FIG. 3, a battery pack 300 can be provided in a suitable size, such as, but not limited to, a 1×, a 1.25×, and a 1.5× size, for example. An on/off switch 202 is used to power an LED light or other illumination source on the selected tool. A wireless transceiver 120 can be provided on handle 110, as described in more detail subsequently.

An extension wheel 204 can be used to move the selected camera system or coupled tool forward or backward along the direction of the shaft 118. The tool being moved by extension wheel 204 manipulation can be selected using tool selection toggle switch 200. Distance moved can be shown on display 102. When the tool is in piercing tool mode, extension wheel 204 can be used to control opening and closing of the piercing tip.

Figure 4:
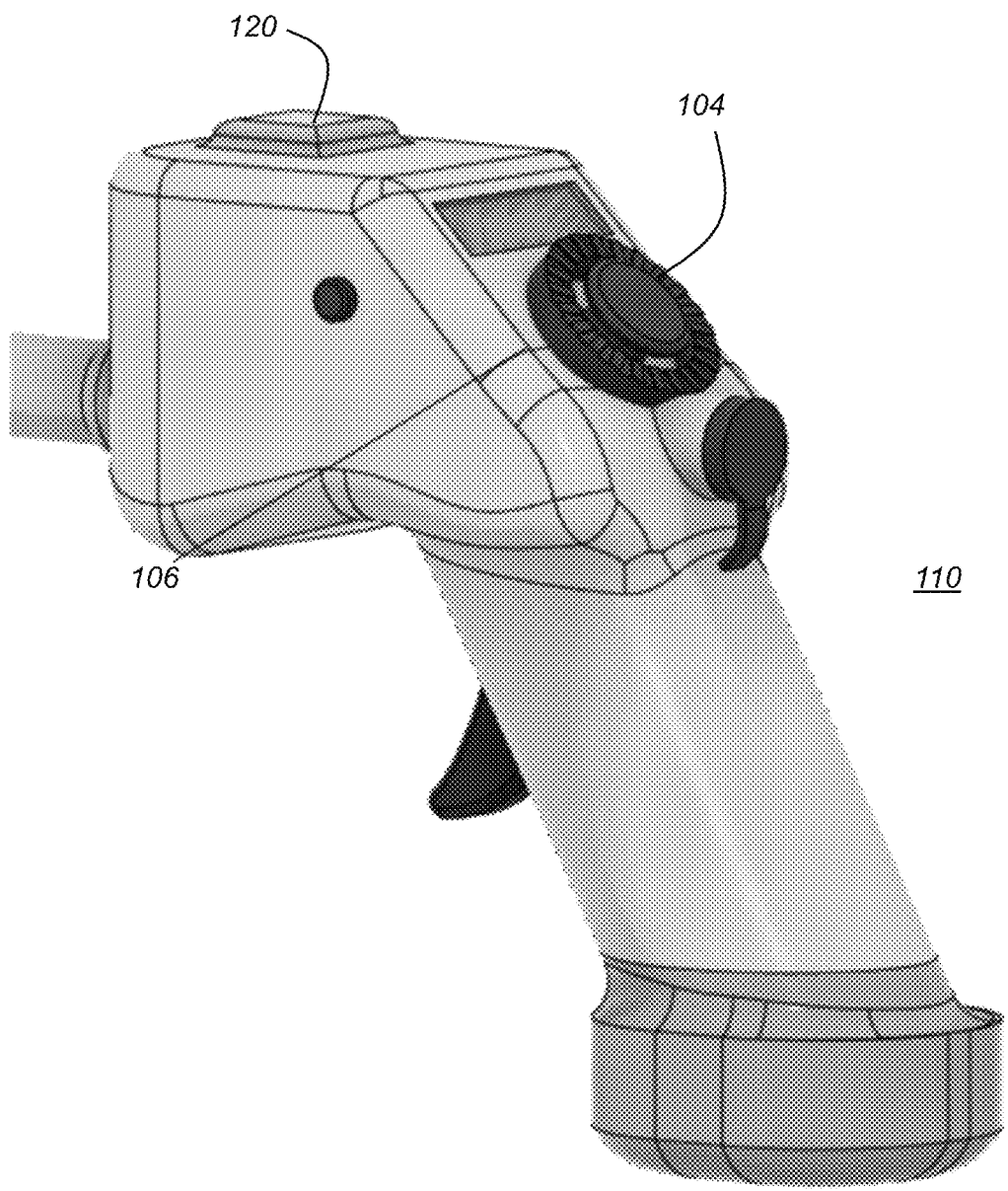
FIG. 4 is a perspective view showing the swivel-camera laparoscopic tool viewed from the left side of the handle according to an alternate embodiment of the present disclosure.

FIG. 4 shows handle 110 in an alternate embodiment, wherein optional control roll wheel 106 is formed around the circumference of control 104.

Figure 5:
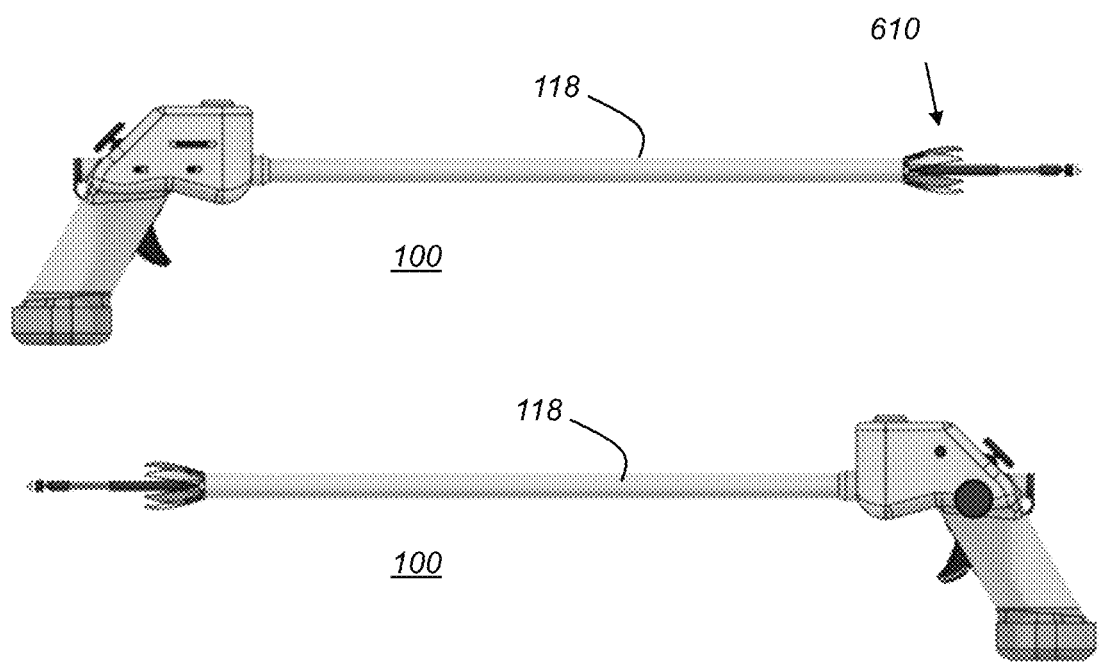
FIG. 5 is a side view that shows each side of the laparoscopic tool according to an embodiment of the present disclosure.

FIG. 5 shows alternate left- and right-side views of a laparoscopic apparatus 100 according to an embodiment of the present disclosure.

The handle 110 housing may also include one or more of a main circuit board, auxiliary circuit boards, connectors, circuitry, controls, digital display, LED illumination, wireless module or circuit mounted chipsets, power and a battery charging circuit disposed therein.

The battery charging circuit can be configured for charging the at least one battery internally and at least one battery which is charged either wirelessly, while still attached to the handle, or the at least one external battery may be disconnected to be charged at a remote charging station. An internal battery power management system can accomplish a number of functions. For example, internal power management can charge and regulate both the internal and external battery/batteries. Internal power management can also provide a continuation of a visual feed and electronic controls if an external battery is "hot-swapped" during surgery.

The handle 110 subsystem at the proximal end couples to the proximal end of shaft 118 housing. Connectors (not shown) on handle 110 provide coupling to suitable power sources, signal connections, or mechanical connections suitable for each type of laparoscopic tool. At the end of the shaft 118 is a retractable obturator with mini-trochar blades to pierce skin and tissue to permit the device to be used inside the patient's body. Once inside the body, the obturator subsystem can then either simply open or even retract to permit the internal barrels to operate.

The trochar blades may be opened and closed using handle 110 controls on the proximal end of the shaft 118. When both gimbal and twist (rotate) functions are actuated using controls, such as the toggle switch and wheel control in the embodiment shown herein, the camera can move 360 degrees by 270 degrees, as shown subsequently. The apparatus can be controlled to permit the trochar blades to rotate about a rotation axis that is parallel to the longitudinal center axis (z axis) that extends through the shaft 118.

Tool and Tip Options

Figure 6:
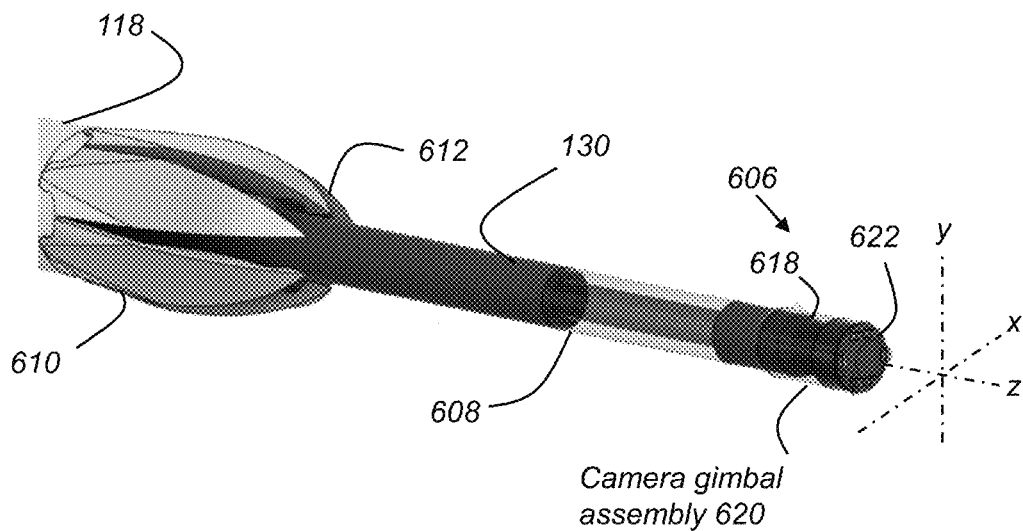
FIG. 6 is a perspective view of a single-tool tip according to an embodiment of the present disclosure.

FIG. 6 and following show a number of laparoscopic tools that can be coupled to laparoscopic apparatus 10. FIG. 6 shows an opened trocar piercing tip 610 wherein shaft 118 supports a single-laparoscopic tool. Piercing tip tool 610 is designed for insertion into the body. Trochar teeth or blades 612 can be opened and closed using extension wheel 204 shown in FIG. 2 or other suitable control mechanism. An inner axial tube 130 within shaft 118, shown centered on the z-axis in FIG. 6, can be rotated a full 360 degrees about the z-axis using roll wheel 106 (FIG. 1). An LED guide bar 608, housed within shaft 118, can provide illumination for the body cavity that is probed by tip tool 610. Controlled by an LED on/off switch, LED guide bar 608 can help to prevent errors resulting from shadow effects.

It should be noted that rotation may not be about the center axis of shaft 118. Instead, rotation is about an axis that runs parallel to the center axis of 118.

At the distal end of tube 130 and tool 610 can be a clear housing 606 enclosing a camera gimbal assembly 620, allowing a camera 618 up to 270 degrees movement in both the x (horizontal) axis direction and y (vertical) axis direction. The camera 618 rotational and extension movement can be controlled by the joystick control 104 and by roll wheel 106 movement. The gimballed arrangement allows up to 360 degree rolling (rotation about the z-axis central to shaft 118) and axial rotation about the x- or y-axis over a range of angles, such as 30 degrees, 60 degrees, 90 degrees, 180 degrees, or more, such as up to approximately 270 degree vertical/horizontal field of view. One or more LED lights 622 can be disposed at the tip for illumination of the subject anatomy.

Figure 7:
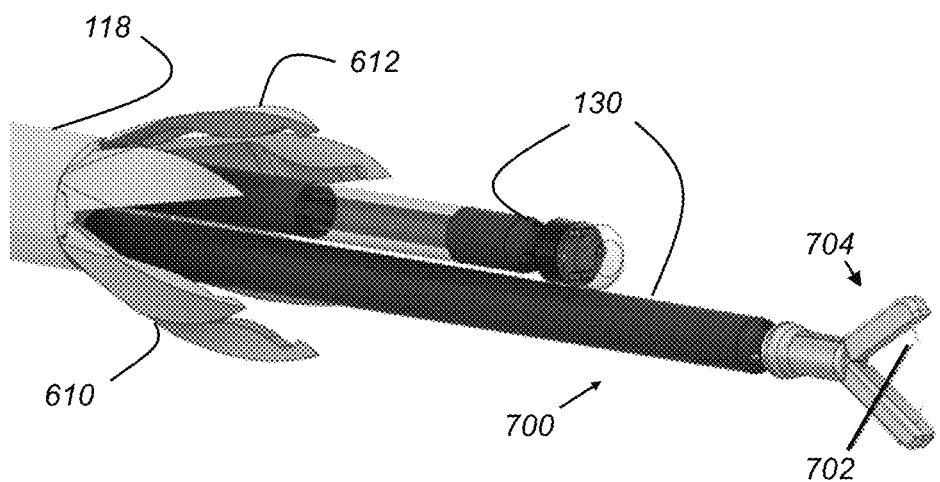
FIG. 7 shows a perspective view of a multi-functional dual tool.

FIG. 7 shows a perspective view of a dual tool 700, which can have any of a number of functions, including but not limited to grabbing, cutting, or extracting tissue or other material. Dual tool 700 can have an extra illumination source, for example. In the FIG. 7 example, a biopsy tool 704 with a needle 702 is shown.

Figure 8:
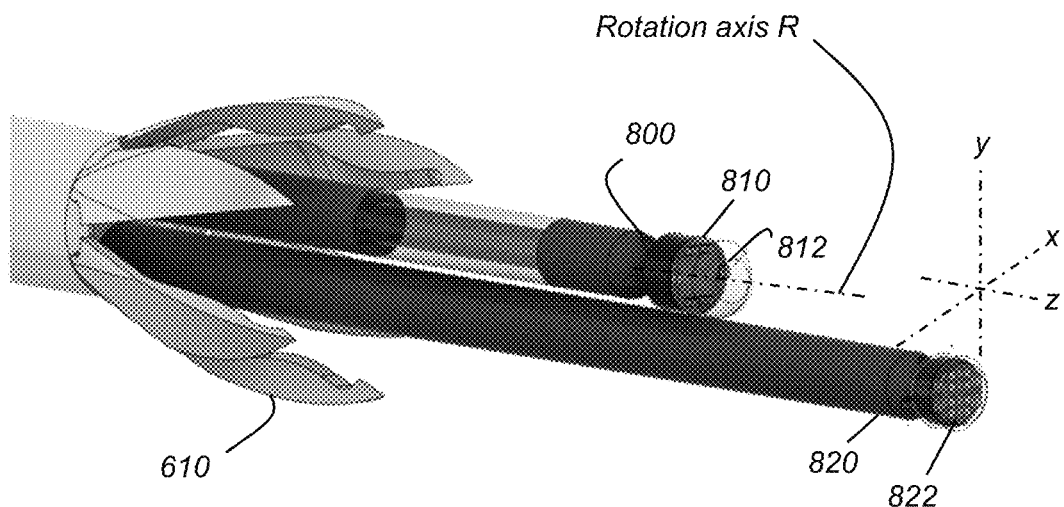
FIG. 8 shows a perspective view of an alternate dual tool.

FIG. 8 shows a camera gimbal assembly 800 that allows 270-degree angular movement about the x and y axis for pan and tilt of the camera and lights. Camera gimbal assembly 800 includes a camera 810 that can be coupled to the distal end of shaft 118 and controlled from the proximal end by joystick control 104 and roll wheel 106 (FIG. 1). Camera gimbal assembly 800 can also include LED lights 812 coupled to the shaft 118 or to camera assembly 800. A second tool gimbal assembly 820 provides an auxiliary illumination tool 822.

Figure 9:
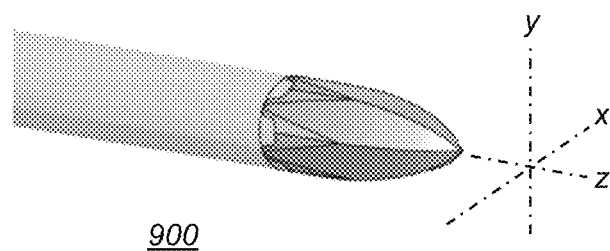
FIG. 9 shows a closed trochar tip according to an embodiment of the present disclosure.

FIG. 9 shows a closed trochar tip 900.

Figure 10A:
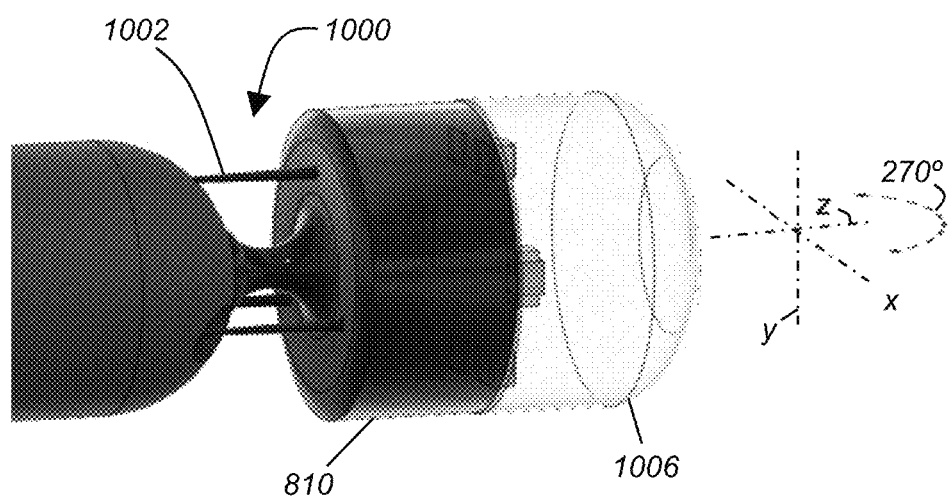
FIGS. 10A and 10B show perspective views of rotation and gimbal motion for a camera mount at the tip.
Figure 10B:
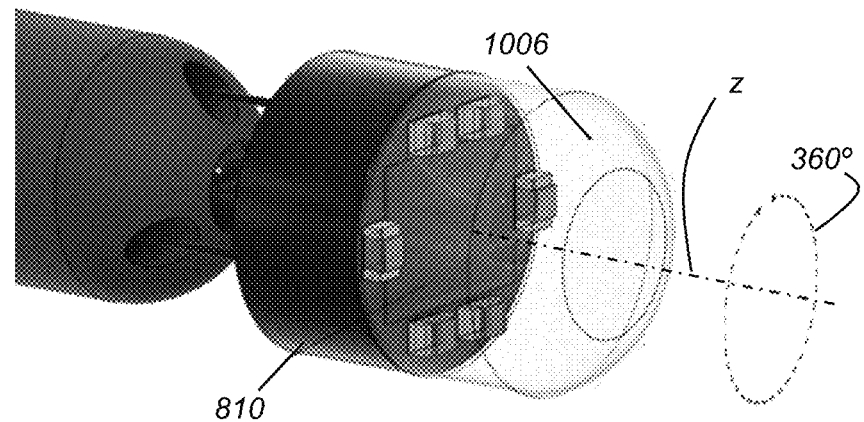

FIGS. 10A and 10B show perspective views of rotation and gimbal 1000 motion for a camera 810 mount at the tip of shaft 118. A three-cable gimbal system 1002 can be used to allow a wide rotation angle. A clear housing 1006 can be provided as shown, to help maintain a clear visual field for the camera and illumination elements.

Figure 11:
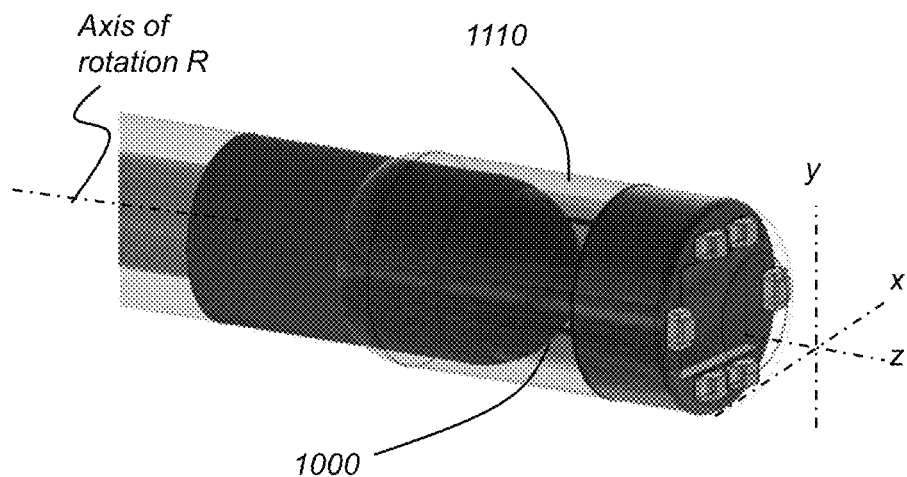
FIG. 11 shows a flex hose enclosure sleeve that encases the gimbal components in order to prevent damage and to keep the system enclosed.
Figure 12:
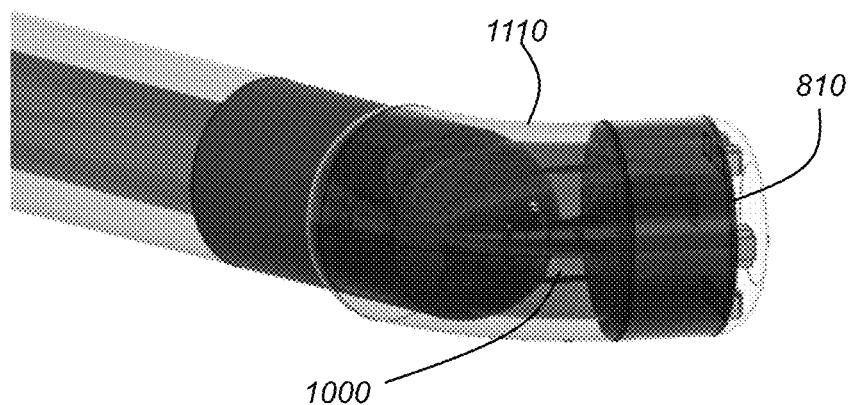
FIG. 12 shows the camera turned from its FIG. 11 position.

FIG. 11 shows a flex hose sleeve 1110 that encloses and protects the gimbal 1000 components in order to prevent damage to the laparoscope apparatus and to surrounding tissue and to keep the system protected from fluids. FIG. 12 shows camera 810 rotated from the position in FIG. 11, with hose sleeve 1110 providing the gimbal mechanism with a flexible seal that allows angular gimbal movement, with full rotation about a rotation axis R parallel to the center z axis and rotation about the y axis for movement in the x-y plane.

Figure 13:
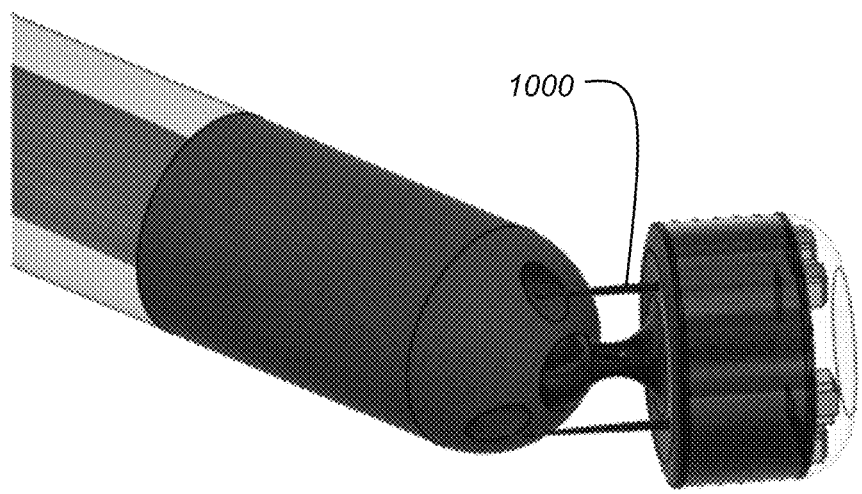
FIG. 13 shows gimbal components with the hose enclosure sleeve removed.

FIG. 13 shows gimbal 1000 turned to the position held in FIG. 12, with hose sleeve 1110 removed.

The device handle 110 is attached to shaft 118, which is inserted into the anatomy as described previously. Within shaft 118 are one or more cylindrical tubes that can move independently from sleeve 1110. The internal tubes provide actuation for the corresponding tool, such as to provide electrical power and communicate signals to and from the tool or to provide mechanical movement, such as from an internal cable, for example. Internal tubing can extend, or be extended, beyond the distal edge of the cylindrical shaft 118.

In one embodiment, cylindrical shaft 118 diameter can be as small, such as 8 mm diameter, and can contain a single tube 130 that provides a camera sub-system within either a rigid or flexible housing. One important advantage of the small 8 mm diameter relates to incision size; typically, an incision formed for accepting this smaller diameter can be small enough for healing without the need for a suture.

At the distal end of the shaft 118 is a retractable obturator or trochar piercing system 610, as shown in FIGS. 5-9. This system has a sharp head and is made of retractable blades 612, or sections, which can close to collectively pierce the body or tissue for insertion, and then open, or retract into a specialized housing on the external tube, to enable the one or more internal cylinders to operate clear of the blades or by elongation.

A smart extender control permits one or more of the internal tubes to extend up to 100 mm or more (and then retracted) beyond the end of the shaft 118 housing or obturator system.

In another embodiment of the present disclosure, shaft 118 can have more than one internal tube 130 which can hold a laparoscopic tool and can provide actuation stimulus, as well as being configured for control and extension. According to an embodiment, one tube 130 typically holds one type of laparoscopic tool, such as the camera subsystem and the other is used for another type of laparoscopic tool or endoscopic tool such as an insufflator, grasping forceps, bipolar forceps, scissors, biopsy spoon, needle driver, torcher, and cryosurgical tool or any other tool used in surgery.

In one embodiment, the housing has an opening which permits the insertion of the laparoscopic or endoscopic tool.

One benefit of the embodiments described herein relates to the dual tool capability. Using this, for example, a surgeon needing to perform a biopsy of a patient can insert both the camera and a tool such as a biopsy spoon, to image and collect a biopsy with the same device and controlled by the same controller.

In another embodiment, the tube 130 holding the camera subsystem is not stiff, but is flexible, with the degree of flexibility controlled by the controller within handle 110.

Wireless Communication Features.

The Applicants' laparoscopic device can have WiDtrx™ modems (Ocutrx, Orange County, CA) that create a wireless link between tools and data inside the body cavity or extant in the OR. This enables the Scopetrx laparoscope or other laparoscope apparatus according to an embodiment of the present disclosure to transmit high-speed video content, such as 4K HD video feed, wirelessly with a latency rate of less than 7-11 milliseconds, which is approximately the same as a wired system or HDMI (High-Definition Multimedia Interface). In addition to surgery, the Applicant's WiDtrx modem, or other suitable modem, can be used for a wide range of applications from wireless docking, multimedia streaming, high speed data transfer between devices, telemedicine, and other networking applications.

The receiving counterpart can be mounted in a monitor, including a virtual reality type device such as the ORLenz™ Augmented Reality Surgical Visualization headset, or on other suitably configured augmented reality headset, so that it will be as close to the headset as possible, as well as in a stationary position in the operating room.

The circuitry in the handle 110 housing includes one or more wireless transceivers 120, each capable of wireless transmission of data and video information from the device to a remote location where it can be received and displayed. The wireless transceiver 120 is configured to convert an optical image produced by the camera sensor into an electrical signal. The signal is wirelessly transmitted to a wireless receiver positioned remotely from the handle 110 housing.

Handle 110 also houses one or more antenna for sending and receiving wireless data and video. The wireless system may also include an input module for control sent remotely.

Wireless communication may also be accomplished through optical communication or through radio-frequency (RF). RF requires a transmitter and a receiver or a transceiver that incorporates both transmitter and receiver. RF communications may be used over a proprietary or a predefined protocol such as Zigbee, Bluetooth, Bluetooth Low Energy, Z-wave, or Wi-Fi. A transmitter module is an electronic sub-assembly that is capable of transmitting a radio wave and modulating that wave to carry data. A receiver module is also an electronic sub-assembly that receives a modulated RF signal and demodulates it.

The wireless technology may also employ video over IP, also called streaming, using existing standards or proprietary methods for encoding the material into a bitstream, and then using an internet protocol (IP) network to carry that bitstream encapsulated in a stream of IP packets. A bitstream is a sequence of bits. A bit is a basic unit of information in computing. A bit represents a logical state of two possible values, which are most commonly represented as a binary digit: 1 or 0. Because of the sequential nature of the video signal, resending packets is typically not an option. Additional error correction information may be added to the data transmission to ensure the stream can be reconstructed even if a few packets are lost in the transfer.

While Wi-Fi IEEE 802.11 may work, the best method to obtain higher speeds that equal HDMI (High-Definition Multimedia Interface) transmission may be to use a method so that uncompressed video can be sent from the laparoscopic instrument's image processing system to the AR/XR headset. In the preferred embodiment, a digital buffer may be acquired from the camera sensor as translated and augmented with the extra overlay information, if applicable, by the computer controller system, then the digital buffer may be transmitted uncompressed to receiver, which may be in the AR/XR headset. When the uncompressed data and buffer is received by the receiving system, it may then be translated to a pixelized image as a sequence of the streaming video. In the event of a problematic transmission where the checksum is off, then that frame may not be displayed and instead discarded or held for future reference. In addition, the program may freeze any buffered frame for hold until a valid frame was received.

In addition, the laparoscopic instrument may include a 5G modem to be capable of edge computing at multi-gigabit speeds. 5G multi-access edge computing (MEC) is a technique to migrate computing and traffic from a centralized cloud to the edge of a network, such as a localized mini datacenter where all computing is on-site or with a geolocated data center near the physical location. Data is collected and processed near the location reducing latency and providing real-time performance for high bandwidth applications. The wireless software may leverage existing wired/wireless networking infrastructure to achieve interactive low-latency peer-to-peer connections. Additionally, the Handle may include a cellular module so that information may be sent via cellular RE, especially considering the close applications of 5G Multi-Access Edge Computing, which would permit ultra-fast sending or receiving of remote information by 5G.

The laparoscopic instrument may be connected with some or all its components and viewports to a hospital, clinic, or other 5G MEC system in a healthcare or training setting, so that the system may support a video feed for multiple users and with the 5G reliability increase the throughput supports massive data transfers, latency is reduced, and throughput of data is increased to a projected 100 Mbps with potentially greater than 10 Gbps peak speeds. Latency is a time interval between the input to a simulation and the visual or auditory response to this input. The laparoscopic instrument system may have dual redundancy, including wire and wireless, and may comprise a sending modem in the handle of the system.

Optical Frequency Wireless

Low latency video transmissions may be required for useful video streams for real time laparoscopic surgery feeds. This latency may be defined as less than 20 ms. Uncompressed video data transmission may be required to achieve these latency numbers. Typical wireless video transmissions may include some amount of compression so as to fit the entire video stream in the usable throughput of the data transmission system. The incorporation of certain data transmission technologies, however, may allow a much higher amount of data to be available for the transmission of high-resolution video. Using a free space optical system, the system may achieve data rates high enough to transmit uncompressed video data, which can be in excess of 20 Gbps for up to 4K video with 10-bit color. The system may utilize multiple optical receivers on the headset, which may each have a different range of directionality so as to have a wide field of reception. The system may also utilize a transmitter that utilizes special tracking in real time in order to align the relatively narrow beamwidth of the transmitter to the receiver array on the which may be affixed on the ceiling of the OR or on a stand. In another embodiment of the invention, a system could be used that utilizes active alignment on both the receiver and the transmitter.

Display

According to an embodiment of the present disclosure, control information is show on the device display, while the video from the one or more cameras feed and other data can be sent to a display device, such as, but not limited to, a head mounted AR/XR headset, like the ORLenz™ Surgery Visualization headset from Ocutrx, Orange County, CA, or to one or more monitors, or to a virtual reality type device, or to any other device, such as the OR-Bot Surgery Visualization Theatre, capable of receiving and projecting data and video.

To access digital information while performing surgery, the surgeon can bring this information onto the lens by activating visualization software, such as, but not limited to, the MedTiles software from Ocutrx, Orange County, CA

Gimbal Mechanism

Tubing 130 which supports the camera subsystem is rotatable within shaft 118. The camera tubing 130 can be turned 360 degrees about a rotation axis parallel to the longitudinal center axis for obtaining a better camera angle, by the control on the handle 110, such as using an alternate position of the toggle switch for the joystick, a wheel control, or other control device.

The camera and lens module can be mounted on a gimbal mechanism at the end of shaft 118, providing a pivoted support camera module that allows the rotation of the camera to approximately 270 degrees about an axis that is orthogonal to the central z axis of the tubing 130. The gimbal system can be actuated by tiny servo motors that move the cable mechanism that causes the camera module to pivot. In an embodiment according to the present disclosure, there may be one or more cameras mounted on the rotation sub-system. According to an alternate embodiment, a pair of cameras can be disposed at an offset for stereoscopic imaging, thus obtaining image content for forming a 3D image.

Controller

A non-transitory model view controller is used to control the device. Other components may include additional central processing units, one or more graphics processing units, one or more digital signal processors, firmware, hardware, software, and/or memory components, as well as other desired components, including a non-transitory model view controller. An operator may input the appropriate settings and model control system may utilize a keyboard, a connected Bluetooth device, or the controls on the handle.

The controller and software may employ bidirectional communication between a host/server and a client to transfer data, images, and telemetry information between the two devices, virtual or physical, for display on any of the viewports. The laparoscopic instrument's controller and software may handle remote inputs, which may be sent back to the server and evaluated or executed. This may enable high-performance computing to be processed remotely by one or more high-powered networked servers through the cloud or on a localized network. This methodology may work on wired, wireless, and cellular networks such as 5G MEC. The controller software may enable cross-platform users to efficiently render the incoming frames using a variety of coding libraries, such as OpenGL or Metal. The laparoscopic instrument may support Windows, MacOS, x86-64 Linux, Android, iOS, or ChromeOS and can be adapted to work with future operating systems.

Camera and Imaging Components

Surrounding the front face of a camera 810 is a set of one or more LED lights for illuminating the area of camera focus. In addition, there can be one or two cameras or one or two camera sensors (wherein the balance of the camera mechanism can be housed in the handle) mounted in the distal tip. Two cameras, if used, can be affixed in a parallax position in order to create a 3D image capable of being viewed in any of the 3D displays mentioned herein or otherwise. When two sensors are used to create a 3D image, they can be positioned to create two virtual images which present a binocular disparity so that the resulting imaging is stereoscopic and seen in 3D. Then the signal from the dual sensors is communicated over separate channels to the handle, where the image sensor processing (ISP) is housed, along with controllers for adjustment of the apertures, focus, digital zoom, and the overlay of other virtual information on the real-world 3D imaging.

Figure 14:
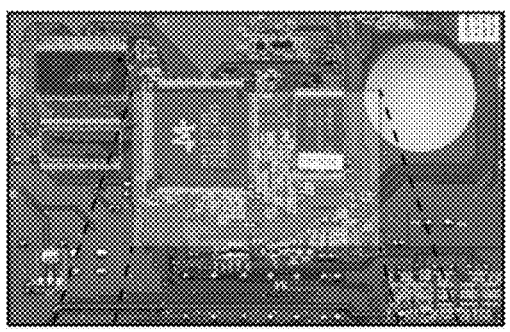
FIG. 14 shows a method by which digital zoom is created.
Figure 14:
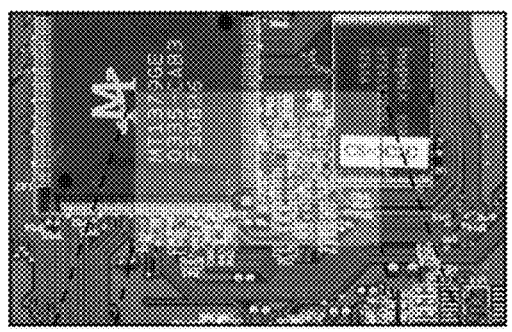
Figure 14:
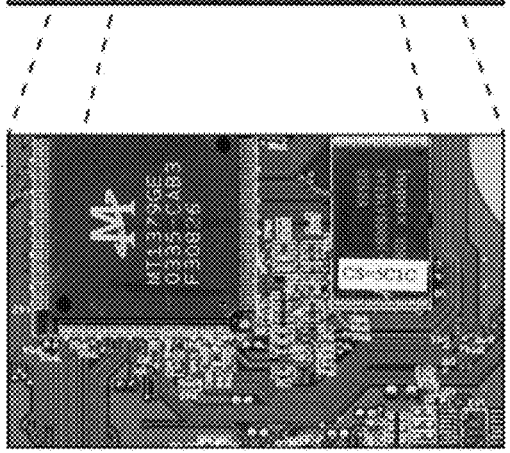
Figure 14:
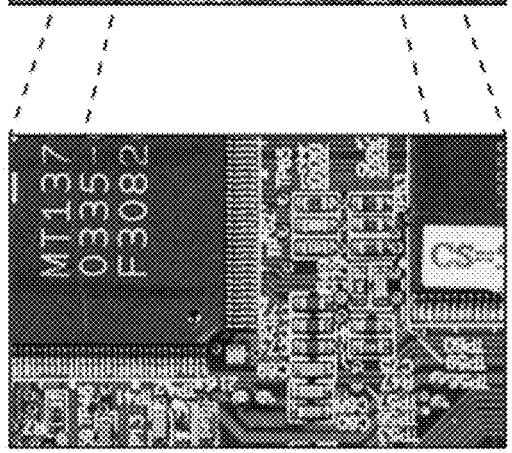

The image captured by the sensor(s) can be magnified to improve detail visibility for the surgeon. To accomplish the digital magnification, digital cropping is used to provide digital zoom. As shown in FIG. 14, "Digital zoom" is a method of decreasing the precise angle of view of a digital photograph or video image by taking a subset of the pixels. Digital zoom is accomplished by cropping a subset of the pixels from the original image 210 while keeping the same aspect ratio on the subset image 212 as the original, and then scaling the subset image 212 back up to the original dimensions the of the original image 210. These processes can be repeated until the resolution is so low that the picture quality does not justify further digital zoom magnification; the image can then be cropped and enlarged; the image can be presented with the same pixel size of the sensor(s). This is typically when the same resolution exists in the cropped and enlarged image as is extant in the display(s) used. For example, this occurs when the final cropped and enlarged image 214 is 4K (3,840×2,160 at 16:9 aspect ratio) and matches the display resolution.

Figure 15:
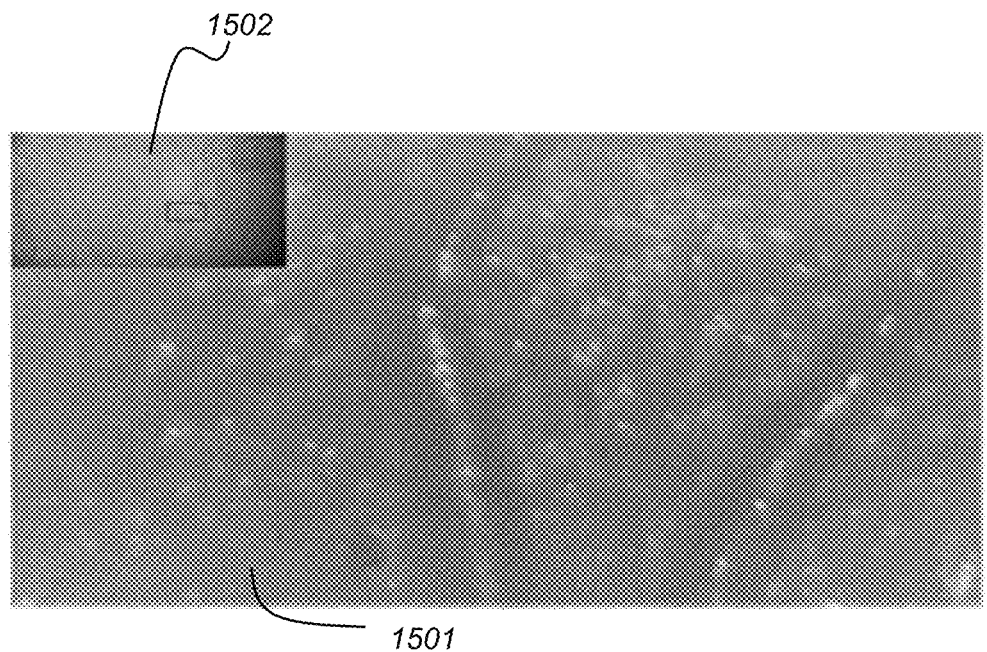
FIG. 15 shows how a Picture-in-Picture is represented.

FIG. 15 depicts a picture-in-picture (PnP) feature of the Scopetrx device. When the surgeon begins to zoom in or magnify an image or area, the controller may be prompted to begin creating a picture-in-picture which may appear, with one image 1302 within another 1501. The PnP may allow the viewer to keep a particular orientation, allowing the viewer to maintain orientation to the larger structure and environment.

This utility is designed to simplify identifying where the viewer is in relation to the non-zoomed image. This feature may permit the surgeon to examine the same region of the image with different zoom levels or different angles, with respect to the whole image before it was magnified.

Through software and the controller, each picture may be a dynamically linked map that follows along the same coordinates. Changing the coordinates of the center on one of them may lead to an automatic displacement of the center in the same point of the second and a coordinate display unit informs of the current coordinates. Thus, when a user begins to magnify or zoom in an image or video, a secondary picture may appear on the lens of the viewport and the larger, magnified image may become the primary picture.

The primary picture may be magnified as specified by the user while the secondary picture may capture the original coordinates of the primary picture before it was magnified. Through software control and menu selection, the secondary picture can be pinned to either the top left corner, top right corner, bottom left corner, or bottom right corner depending on the surgeon's preference, or as a preset, and can be shifted to a new location using touch commands on the internal display, which may be a touch screen, or by other control The secondary image may be a digitally altered subsampling of the primary image. Thus, the secondary image may fill the viewport showing an inspector their region of interest, while the primary image may be placed in a corner of the viewport to serve as a map. The position of the secondary image may then be indicated on the primary image via an overlay, whether varying capacity monochrome or color. Digital altering of the primary image can include digital zooming, color contrast enhancement, color picking, or other video processing system that is useful for the surgeon.

Picture-in-picture technology in the laparoscopic instrument may permit a surgeon or user of any of the 3D displays mentioned herein to watch two images or videos (primary and secondary) simultaneously. Thus, the surgeon could simultaneously see imaging from two separately placed laparoscopic instruments. The primary picture may fill the entire screen or projection across a display, while the secondary picture may be a smaller (approx. $1/4^{th}$ of the primary picture size), floating window pinned to a corner of the screen (always on top of all other windows), which may allow users to keep an eye on what is happening in both images at one time. This may be especially helpful if the surgery is near or adjacent to an especially vulnerable organ. Thus, the surgeon could see the (larger) image of the cutting, ablation, or resecting, which watching from another angle to how close the instrument is to a vital or vulnerable organ.

In addition, to reduce the signal noise so that the quality of the image remains as sharp as the original, pixel-binning may be used. Pixel-binning is a process where a clocking scheme is used to combine the charge (light) collected by several adjacent pixels to reduce the "noise". Noise in this instance is random variation of brightness or color information in images and is usually an aspect of electronic noise which is created by the digital camera sensors. To correct for this "noise" upon digital magnification pixel-binning is used whereby you can obtain the best detail in good lighting conditions, while also being able to produce high-quality low-light shots. The high-quality low-light video or images is created by sampling multiple pixel's light. The sensor or sensors chosen for the microscope contain the largest pixel size possible or available. Thus, with the larger a sensor's pixels (or photosites), the greater their light-gathering ability, which is axiomatic. However, it takes a lot of pixels to render in high resolution. The size of a photosite is called the pixels' 'pixel pitch', which is measured in microns. Thus, a larger micron pixel has a higher pixel pitch. Because not all photosites collect the same amount of light (red, green, and blue) pixel-binning is used to sum the signals of adjacent pixels to enhance the resolution and increase the signal to noise ratio. The resolution is enhanced because the higher the signal to noise ratio, the clear the definition is and the more the boundaries between different color and brightness of the pixels is evident. Thus, the combination of digital zoom and pixel-binning permits the zoom feature to go far beyond what optical zoom alone can do. This is one of the major benefits of having digital zoom.

Both the digital zoom and the pixel-binning are accomplished by digital signal processing, typically done in the CPU in combination with the GPU. Also, a technique called "image thresholding" may be used to enhance a part of an image that is the focus of interest which in combination reduces background imaging, so that the net result is that the portion of the image which is of interest is more clear and easier to evaluate.

Through digital image processing, thresholding is a method of segmenting images. From a grayscale image, thresholding can be used to create binary images. The simplest thresholding methods replace each pixel in an image with a black pixel if the image intensity is less than some fixed constant T or leave the pixel unchanged if the image intensity is greater than that constant. So that if the pixel constant is less than T it is set to zero.

The device may also include the additional technologies of sub-pixel colors and contrast modification from the image capture sensors accomplished in the software using such computer vision techniques as: thresholding, texel (a textel pixel is the fundamental unit of a texture map which are obtained through simple procedures such as thresholding) and dextel classification and modification, color detection, object detection, semantic segmentation, thresholding, and negative imaging. This is made possible by the potential colors and the resolution of camera sensors which may detect colors, and differences in colors, some not even distinguishable by the human eye.

In addition, digital signal processing can be used and enhanced by Artificial Intelligence (AI) whereby algorithms are used to identify structures (patterns, i.e., trace lines in a circuit board or known components on a circuit board) within the image and/or patterns within the pixels and augment to create a vector shape around a fuzzy line (such as a trace) to correct the fuzziness. In addition, AI can include a background subtraction which removes black light by pixel subtraction. The pixel subtraction is a process which takes two images as input (as in the case of the two images with 3D) and produces as output a third image whose pixel values are simply those of the first image minus the corresponding pixel values from the second image. This can be helpful to the surgeon to delete items from his that are not necessary for the surgery, i.e., other laparoscopic instruments and non-functional tools.

It is also possible to use a single image as input and subtract a constant value from all the pixels through AI, or the AI could produce an output which is the absolute difference between pixel values, rather than the straightforward signed output.

AI can also be used for image or semantic segmentation, Semantic which is the process of associating each pixel of an image with a class label, such as organ, tool, blood, trocar, etc. The goal of the semantic image segmentation is to label each pixel of an image with a corresponding class of what is being represented and predicting for every pixel in an image is called dense prediction. In computer vision pixel-wise dense prediction is the AI task of predicting a label for each pixel in the image. The reason for dense pixel prediction is so that the intelligence in the system, the model controller, can more effectively highlight, subtract, modify, change color, reposition, magnify, or add text to an image or portion of an image. In this fashion, if there is a vulnerable organ or location inside the body, a text overlay could caution the surgeon about this area.

These processes may also be used in connection with or as a part of the Virtual Mapping and Guidance System described below.

The camera sub-system is adjustable using either the wheel control (360 degrees rotation) or the joystick (camera swivel 270-degree pivot) so that the surgeon has a view not only straight ahead, but can see around corners, organs, and tissue.

The flexible cable within tubing 130 that controls camera position adds to the ability of the surgeon to flexibly maneuver the camera within the body cavity, thus having all the axis flexibility of the rotation of the camera tubing 130 about a rotation axis R parallel to the longitudinal center axis for a full 360 degrees, combined with the capability for in-plane camera angle adjustment of 270 degrees; this angular movement capability is combined with the ability to 'snake' the camera into the body via the flexible cable. In this embodiment, the flexible cable within tubing 130 can be controlled by servo motors which are controlled by the surgeon via the handle controller or remotely.

The controller handle 110 has a number of buttons and other controls that allow maneuvering of tool position and control of tool function. These controls can include a joystick and a wheel controller, as well as other control devices as described previously with respect to FIG. 1. Alternatively, the options on the Scopetrx laparoscopy apparatus can be from a remote location, wirelessly sending and receiving instructions. In a typical configuration, the joy-stick can control the in-plane rotation of the camera subsystem, and the wheel controller can control the 360-degree axial rotation of camera tube 130, as well as controlling the installed tool.

The shaft 118 with either a 12 mm or an 8 mm diameter comprises the housing which is to be inserted into the body. Cylindrical shafts can be included in the device, one for housing the camera and lighting technologies, and the other to support the insertion of laparoscopic tools. In one embodiment of the disclosure, a permanent tool, such as a biopsy spoon, is attached to the tool shaft.

FIGS. 10A and 10B show perspective views of rotation and gimbal motion for camera mount. To encase and protect gimbal and rotation components, the tip is provided with flexible sleeve 1110, as shown in FIG. 11. All tubing, including shaft 118, can be formed from biocompatible material and affixed for removal for autoclaving. FIG. 12 is a perspective view of the tip showing the flex hose sleeve 1110 with camera swiveled on gimbal 1000.

Virtual Mapping and Guidance System

Figure 16:
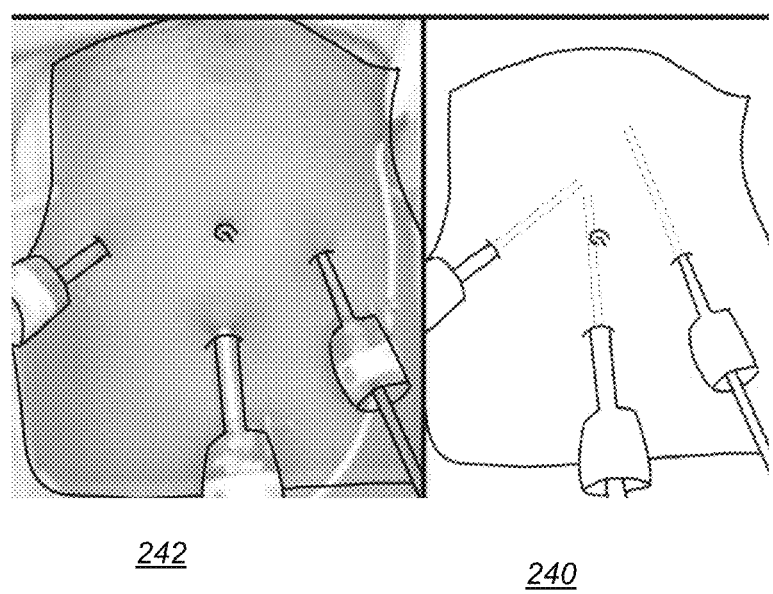
FIG. 16 shows a Virtual Mapping and Guidance System overlay on a patient.

It is needed in the performance of laparoscopic surgery to understand where the laparoscopes (one or more) tools and organs exist inside the body. Currently, the laparoscopic surgeon only has a limited view of the surgery site and that only from one or more cameras inside the body cavity. It is helpful, then for a surgeon who is wearing a AR/XR headset to be able to see a "map" of the surgery site inside the body, while also being able to see the body from the outside. FIG. 16 shows display of a map 240 with a patient 242 in view. Thus, this present invention teaches a method of creating a virtual mapping and guidance system, which is virtually displayed on the AR/XR headset or on an autostereoscopic 3D monitor.

One of the most important features of the Virtual Mapping and Guidance System (VMGS) is body cavity spatial awareness which enables internal structure mapping positioning of the instruments and laparoscopy thereby creating a collision avoidance system and a better understanding of the overall surgery site. Depth estimation is a crucial task in developing a collision avoidance system inside the body cavity.

The traditional approach to depth estimation uses stereo cameras calibrated intrinsically and extrinsically to be used together to understand depth. With two cameras the depth of any point (or subpoints as represented by each pixel) the cameras can view is measured by comparing the pixels related to this point on both the left and right sensors. Or, the camera sensors can affix the depth of any and all pixels in the field-of-view (FOV) which builds, in the software, a three-dimensional grid of the space and objects the camera is recording.

Primarily, the depth calculation is done by computer vision algorithm technologies. The computer vision software uses the parallax error between the images or pixels on the sensors to calculate distance. Thus, a single image or frame of a video is recorded from two different viewing angles, such as the 3D stereoscopic parallax, and, when calibrated, can determine depth as is estimated from the measure of parallax error. Thus, the depth of a point on one sensor is inversely proportional to the distance between the secondary image of this point.

Depth can also be calculated by introducing a triangulation method or a phase shift algorithm. In addition, a time-of-flight sensor can measure the time it takes light to travel from the system to each point of the object for higher accuracy. The present invention may use one or more of these technologies.

Alternatively, depth estimation may be calculated by the use of a single camera sensor when combined with positional data. This positional data is commonly represented as vector data, which is a form of data that represents vertices and paths. This process can create accurate mapping by comparing the differences in images captured by the camera at different locations inside the body cavity. The first feature of the VMGS system is that it is real-time, or within a few milliseconds of real-time, and one or more laparoscopic instruments with cameras in the body are needed to accomplish the mapping and guidance.

At the same time and in combination with the mapping set out above, one may add the techniques of Simultaneous Localization and Mapping (SLAM) technologies to provide the system with spatial awareness of the cameras, instruments, tools and organs in the body cavity in real-time. SLAM means the process of determining the position and orientation of a sensor with respect to its surroundings, while simultaneously mapping the environment around that sensor. This is possible with a one or more cameras, and unlike other forms of SLAM technology as long as there are a sufficient number of points being tracked through each frame, both the orientation of the sensor and the structures in the body cavity can be understood and represented in virtual format.

In addition, the mapping derived from the sensors described above may be augmented using either light detection and ranging (LIDAR), which may or may not be single pixel LIDAR, or by using an additional sensor which incorporates Time of Flight (ToF) technologies. Each of these added technologies add another layer of accuracy and redundancy. These may be housed in the Scopetrx laparoscopic device or be on a separate instrument inserted into the body cavity.

Alternatively, the mapping of the physical organs in the body cavity space can be done prior to the operation by post-processing and in depth of the body cavity. This could be done at the first of the operation with the one or more laparoscopic instrument camera(s), and then stored in memory to be overlaid on the real-time information of where the tools, instruments, and laparoscopic devices with the sensors as discussed above, and exist and move during the surgery.

Using either method, when the system has fully mapped the body cavity and organs along with the tools, instruments, and laparoscopes, in the memory of the system, the system can then use computer vision techniques to combine the image data in their exact or near-exact orientation and spacing. Typically, this would be accomplished by means of visual odometry, which is a part of computer vision, and is the process of determining the position and orientation of an environment by analyzing the associated camera images. At this point everything exists in software. The next step is to use the localization information, such as real-time visual odometry from everything external existing in the body cavity to localize all the laparoscopic instruments, tools, and other instruments to put them in their place inside the mapped area.

The ability to sense the location of a camera, as well as the organs in a body cavity environment, without knowing either data points beforehand is something that SLAM systems are highly effective at, especially when combined with the other techniques as described herein.

Figure 17:
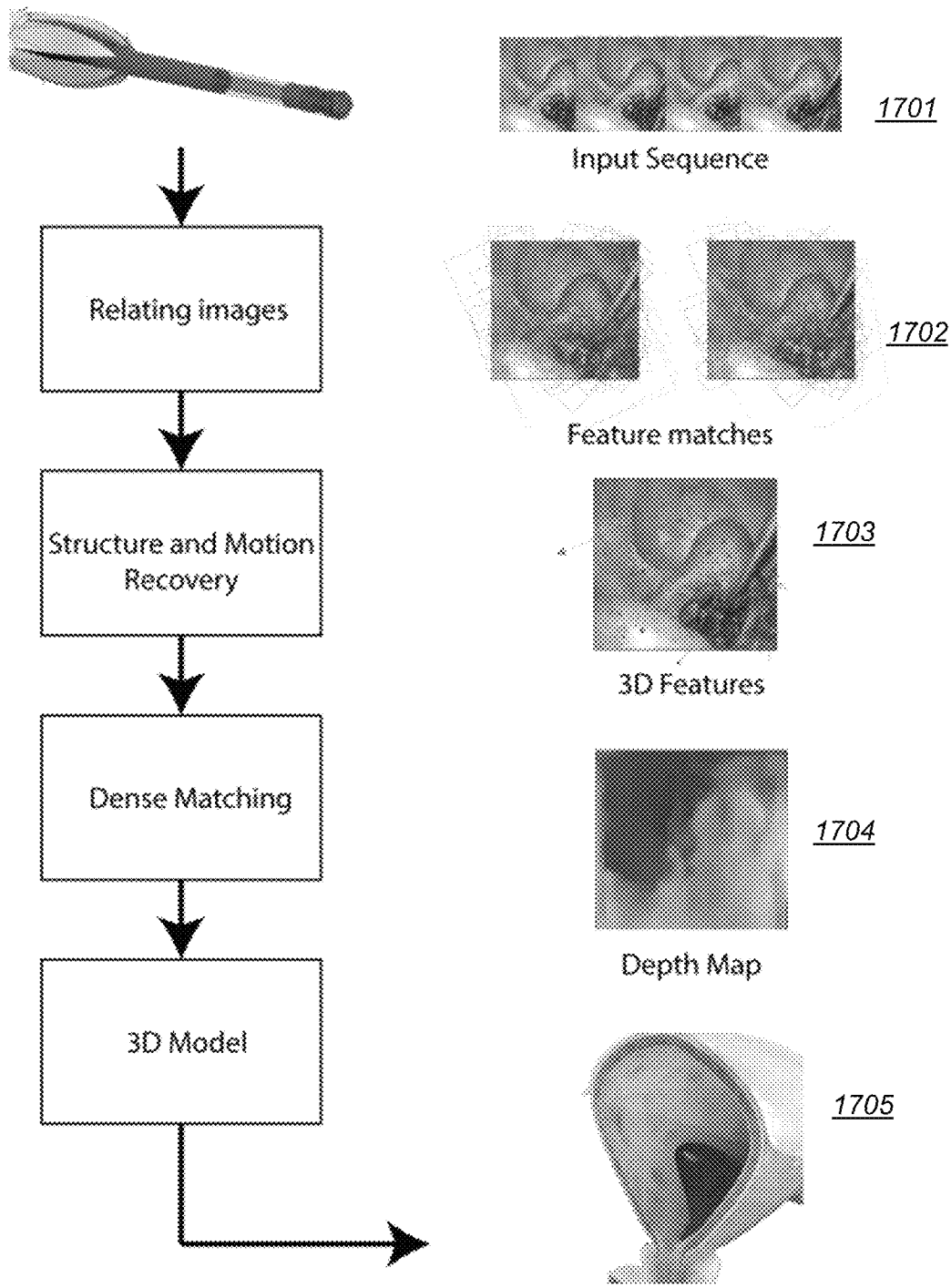
FIG. 17 shows a chart of how a 3D model is created from input sequence of images.

As shown in FIG. 17, the next step is to take all the images as stored in the computer as well as the processed visual odometry from the all the input sequencing 1701, and match related features 1702, then incorporate perspective or the orientation of the camera(s) to the input sequencing, which begins to build correctly corresponding 3D features/point cloud 1703, then the process completes a dense matching protocol, depth map 1704 which aligns the depth of each pixel, which collectively builds a complete 3D model 1705 of everything that exists in the environment. This model is created by the relation of pixels on subsequent images combined with the position of the camera(s) in the position they were when captured. These pixels create a point cloud 1703. The point cloud creates a structure on which the video frames are overlaid. As something moves in the map, each successive video frame displayed to the user updates as instruments or tools in the model move positions.

Then the real-time video information is augmented with the above mapped items and displayed in the AR/XR headset or on a 3D monitor or other 3D visualization method. Thus, when the surgeon is wearing the AR/XR headset he is able to see the outside of the patient and the tools and things which exist outside the body cavity, while at the same time seeing a virtual representation of all the structures and instruments inside the body cavity and see as they move. This real-time modeling and virtual imaging provide guidance to the surgeon on where his instruments are as well as where the structures of the body cavity and organs exist in relationship one to the others.

While the embodiment of this invention may be created either with color or monochrome camera sensors, a monochrome sensor each pixel 8 bits, while in color sensors each pixel has 8 bit each for the red, green blue channels totaling 24 bits. The increase in bit depth from monochrome (8 bits) to color (24 bits) requires increased processing time thus color sensors will result in slower frame. On the other hand, a monochrome sensor can achieve a higher resolution with faster processing.

In addition, this provides the surgeon with collision avoidance mechanism, because the surgeon can see the virtual information, mapped in 3D and spatially corrected, so that the surgeon does not puncture an organ in error or permit the tools inside to conflict on with another. In addition, the system, knowing where each instrument, tool and organ exist, as things move and are updated frame-by-frame in real-time, can also send alerts in the form of audio or visual cues that an instrument is getting too close to and organ or other tool. The surgeon or manufacturer can set tolerances to be tight or loose, depending on the application.

To better understand the real time localization of the instrumentation techniques in addition to those described above, we may employ techniques that would help understand the localization of an instrument by tracking its position outside of the body cavity. While the methods described above relate to mapping and localization of cameras, instruments, organs and other elements inside of the body cavity, we may use techniques to localize the instruments and the camera externally.

Figure 18:
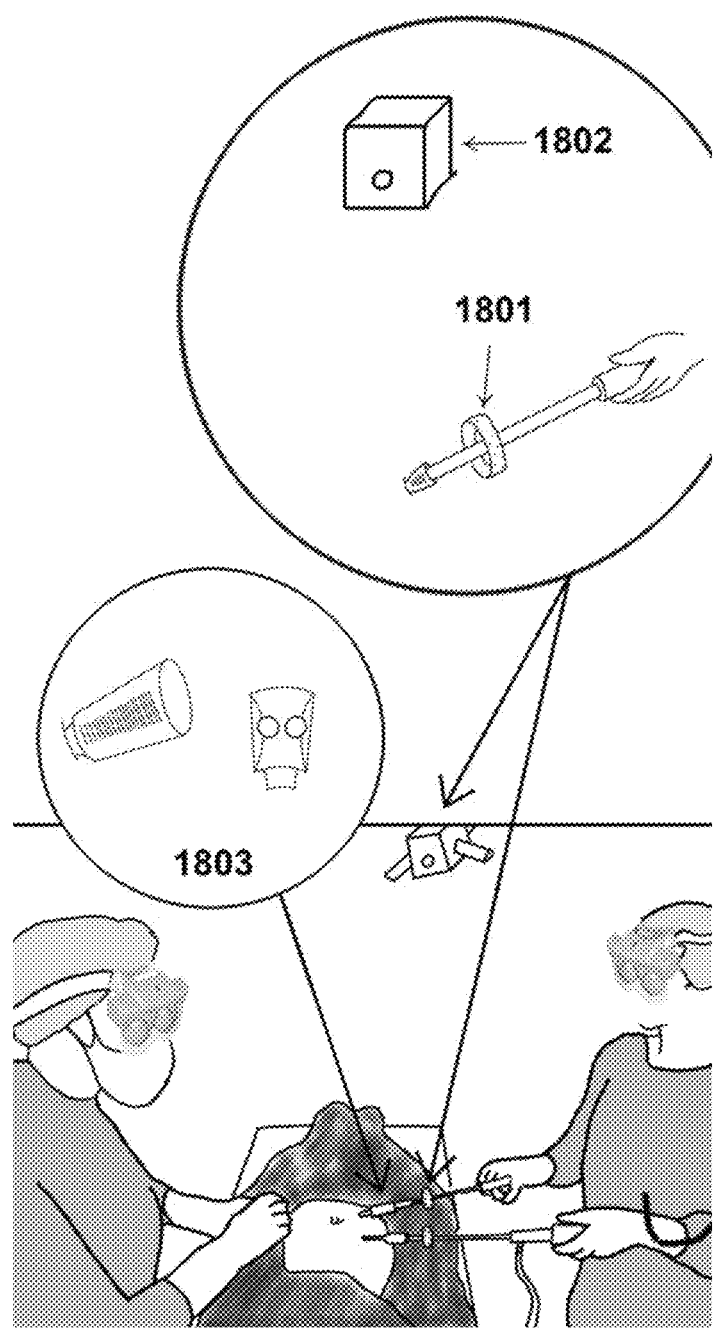
FIG. 18 shows a method by which an imager detects and determines the positioning and orientation of a fiducial marker.

As shown by FIG. 18, one of the methods we employ is using one or more fiducial markers. Fiducial markers 1801 are objects placed in the field of view of an imaging system 1802 to be used as a point of reference to the field of view.

For accurate localization we can use fiducial markers on both the instrumentation, and the trocar for triangulation which will enable the controller to give a position of the instrument inside the body by using fiducial tracking techniques externally.

To understand the specific instrumentation location the instrument must be identified by the system while tracking is ongoing. This can be done by adding metadata to the fiducial markers. For instance, a specific pattern can be associated to a specific tool such as a bowel grasper. Once the instrument properties are understood by the controller, extrinsic localization is possible through fiducial tracking of a known point on the instrument.

Fiducial tracking enables the controller to understand positional data of the instrumentation for precise localization of the instrumentation during the procedure. Fiducial markers are active or passive patterns detected by algorithms in captured images (or video) from sensors for further applications including the automated augmented or virtual reality graphics creation described herein.

Fiducial Markers can be passive, in the form of a camera recognizable pattern, or glyph, but they can also be active in the form of a pattern of emissive IR LEDs or LED's or other light or frequency generator. The medium for translating the data points is computer vision where the image is captured by a light sensing array, such as a video camera or image sensor that is placed in a known position to the procedure. One of the overhead cameras may map the entire surgery site to gain the information of exact positioning of the ports and or trocars to determine RR "anchors" of location, orientation, and scale.

The Virtual Mapping system uses computer vision to analyze images captured by a light sensing array, such as a video camera or image sensor placed, not only in the laparoscopic instrument but overhead, as mentioned above. Algorithms implemented in the controller, or in software, or firmware or hardware, or some combination of software and hardware can provide sensing and identification capabilities based on the positioning of the fiducial marker(s). Computer vision thus permits a digital image (data) or video stream to be identified and correlated from one or more sensor inputs.

In one embodiment, the Virtual Mapping system uses algorithms and information from multiple sensor and data inputs to cross-check and form a redundant set of identified fiducial patters to better estimate the exact location of an item or organ. This permits an automatic dual processing and cross-check for calibration, positioning, and orientation to build the virtual mapping and guidance system. It also provides a redundance for the collision guidance systems and alerts, as well as helps interface with external things like trocars, ports, and machines, such as robotic instrument guidance applications.

As mentioned above, this information can be comprised of all pixel information from a sensor, or from selected or a single sensor to aid in speed and processing. In this way the instrument, tool, or body organ can be first orientated, and then tracked from frame to frame for movement which movement representation is shown in real or near-real time on the overlaid virtual image. Frame tracking is the process of locating a moving object (or multiple objects) in video over time using a camera or other sensor. Thus, frame tracking is an important feature of the virtual mapping system.

In one embodiment, the fiducial markers may be placed around the trocar or "port" device through which instruments are passed into the body cavity. By having one or more cameras located above, either on the ceiling or on a cantilevered holder, so that it is above the patient, the one or more cameras or sensors can recognize the patterns and understand in a three-dimensional way the movement or angling of the trocars as the instruments are passed through the trocars. In addition to fiducial markers such technologies such as (mems) gyroscopes, accelerometers, magnetometers, RFID and GPS technology may exist in the trocars, ports or in or on the laparoscopic instruments or tools used in laparoscopy to aid in creating data points to create the virtual mapping.

To add to the redundancy, a mechanism like a ball bearing type rolling sensor 1803 which may be used in tandem with the canulae portion of the instrument may work together, when calibrated, to track how far an instrument has been inserted, stopped, or retracted from the body cavity. All this information is fed to the automatic controller system which analyzes the information and includes the data points into the virtual mapping system.

Initial calibration of the combined systems, prior to surgery, will ensure that the position of the sensor that is detecting the fiducial markers is aligned with the 3D model that has been created using methods described earlier. This calibration can be done by utilizing the instrument localization described above in the laparoscopic camera (Scopetrx), and realign the coordinates of the extrinsically tracked system based on this method which provides the virtual mapping system with yaw, pitch and roll (x, y, z) information about the instruments, tools and laparoscopic instruments inserted into the body cavity.

Another method of calibration utilizes fiducial markers on the laparoscopic camera to calibrate the system.

The LED Lighting System

The LED lighting system serves several purposes. First, it provides internal light for the sensors to capture the environment. Second, some of the energy from the battery to the LED lights may be "bled" off before the laparoscopic instrument is inserted into the body cavity, permitting the glass or optical plastic housing surrounding the camera(s) and LED lights (and other sensors) to heat up to the temperature of the body cavity, and thus avoid "fogging" of the tool upon entry. Currently, fogging of laparoscopic camera tools is common and can waste up to 15 minutes of each surgery to correct. Third, to compensate for texture-less surfaces, like a stomach or gall bladder, LED lights in various wave-lengths, from ultraviolet and infrared LEDs can be used to project a specific pattern at the same time as lighting the area. By the introduction of structured light or structured illumination, as it is sometimes known, the light is projected known shading pattern which can assist the determination of the exact shape of a texture-less surface. The result is the projection of a known light pattern on the captured scene which can be unsourced in processing. When applied to a texture-less surface the light patterns help make 3D imaging more realistic. The light patterns are created by lenslets on each of the LED's which create a specific pattern. The usage of LEDs for structured lighting is beneficial because LEDs are intrinsically non-coherent, as opposed to lasers, which can create a "speckle effect", which is the actual scattering of coherent radiation, provides the best option. Small lenslets are applied to the LEDs to create the structured light which is removed in post-processing.

This structured light source can be in wavelengths that are detectable by the image sensors which can utilize this data in better understanding the topography of the organs or other elements inside the body cavity but can be filtered or removed from the image seen in real time by the surgeon.

The main purpose of structured light projection is to detect and measure the deformation of the expected pattern on the scene. As an immediate consequence, structured light is used in 3D reconstruction of objects. to reconstruct texture-less surfaces, which are common in internal organs.

Figure 19:
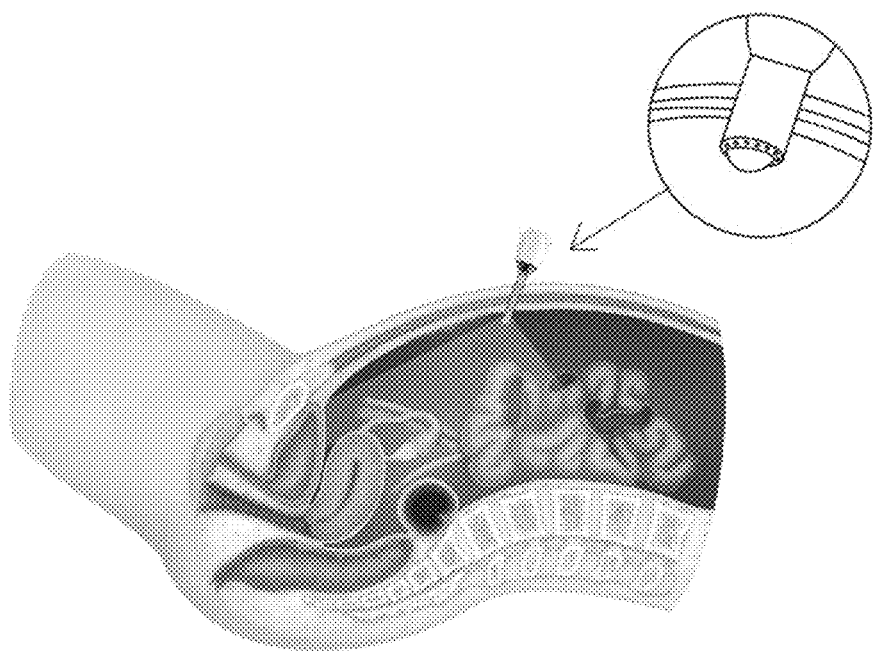
FIG. 19 shows a Trocar Camera Instrument

FIG. 19 shows a trocar instrument in use.

MedTiles Multiple Image Viewing

Figure 20:
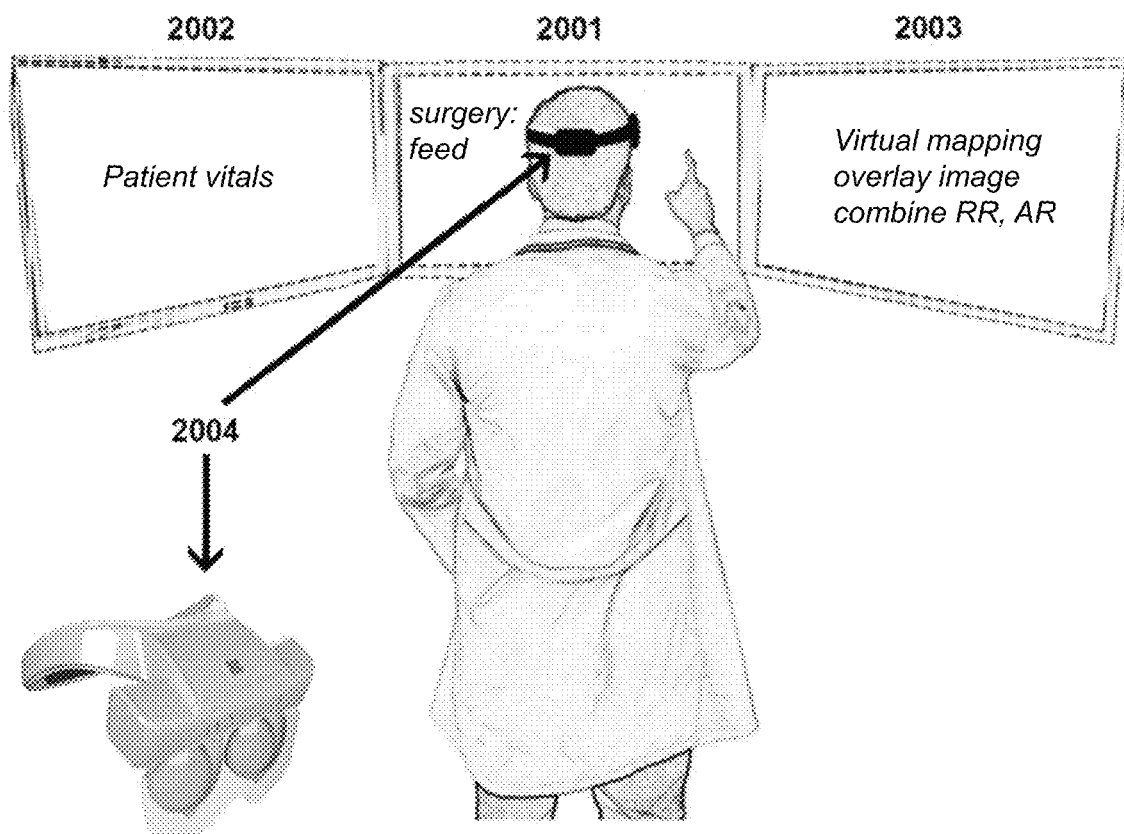
FIG. 20 shows Medtiles Multiple Image Viewing as viewed from an AR/XR 10 headset.

As shown in FIG. 20, if the surgeon elects to view MedTiles display features either on top or bottom of the AR lens, the MedTiles can be rendered in a "horizon" view, meaning the surgeon's gaze can be directed below the horizon for bottom viewing, or raised above the horizon for top viewing. Some surgeons have reported that too much information in the operating room is distracting. Thus, a display utility such as, but not limited to, MedTiles Horizon View is a remedy for this problem, as the surgeon can now keep the field of view feed view free of information until it is needed, and then clear the information once it has been accessed, identifying the information by a virtual hand gesture, voice command or eye-tracking cues. Surgeons will have the option to include text and graph information all the time; or to make a slight eye adjustment when information is needed. In addition, the surgeon can remove the information or can elect to turn off MedTitles completely.

In addition, using the idea of MedTiles™ where information can be virtually displayed in different locations, for instance, (i) the main surgery feed 2001, (ii) information like patient vitals 2002, (iii) or preoperative information such as an MRI or CT scan 2003, which all can be viewed in the AR/XR headset 2004. This information is available to the user by a turn of the head to the left or right, the virtual mapping and guidance system may be also overlayed in the headset such that the surgeon sees what is going on both on the outside of the patient and on the inside. Using the added information from pre-operative CT scans or MRTs the virtual image may include the location and position of internal organs along with the information in 3D of where the instruments and tools are inside in relation to those internal organs.

For instance, if the surgeon elects to view MedTiles either on top or bottom of their lens, the MedTiles can run in a "horizon" view, meaning the surgeon can either lower their eyes below the horizon for bottom viewing, or raise their eyes above the horizon for top viewing. Surgeons will have the option to include text and graph information all the time; or make a slight eye adjustment when they need the information; and to remove the information or can elect to turn off MedTitles completely.

When a surgeon needs to access digital information while performing surgery, he or she can bring this information onto the lens by activating MedTiles.

In still yet another embodiment, the Scopetrx camera subsystem includes one or more batteries disposed within the housing for powering the chip package.

Virtual Mapping and Guidance System

It is needed in the performance of laparoscopic surgery to understand where the laparoscopes (one or more) tools and organs exist inside the body. Currently, the laparoscopic surgeon only has a limited view of the surgery site and that only from one or more cameras inside the body cavity. It is helpful, then for a surgeon who is wearing an AR/XR headset to be able to see a "map" of the surgery site inside the body, while also being able to see the body from the outside. Thus, this present invention teaches a method of creating a virtual mapping and guidance system, which is virtually displayed on the AR/XR headset or on an autostereoscopic 3D monitor.

The map and guidance systems is created by "digital mapping" and computer vision techniques. Digital mapping, which may be called digital cartography relates to the process of collecting and compiling data from one or more sensors, from one of more locations to create a spatially correct virtual image. The purpose of the technology is to produce maps that give accurate representations of a particular area which can be viewed virtually or as a augmented image over a RR image.

Once all the data points are categorized into an identifiable mapping, the model controller can provide additional benefits such as highlight the edges of a surface, an organ, or a thing to be removed or resected, like a cancer tumor, using a superimposed virtual or augmented overlay on the live surgery video feed.

One of the most important features of the Virtual Mapping and Guidance System (VMGS) is body cavity spatial awareness which enables internal structure mapping positioning of the instruments and laparoscopy thereby creating a collision avoidance system and a better understanding of the overall surgery site. Depth estimation is a crucial task in developing a collision avoidance system inside the body cavity.

The traditional approach to depth estimation uses stereo cameras calibrated intrinsically and extrinsically to be used together to understand depth of all the images the cameras capture. These images and shapes and depths which are represented by numbers are converted into 3D images by the software.

With two cameras the depth of any point (or subpoints as represented by each pixel) the cameras can view is measured by comparing the pixels related to this point on both the left and right sensors. Or the camera sensors can affix the depth of any and all pixels in the field-of-view (FOV) which builds, in the software, a three-dimensional grid of the space and objects the camera is recording.

Primarily, the depth calculation is done by computer vision algorithm technologies. The computer vision software uses the parallax error between the images or pixels on the sensors to calculate distance. Thus, a single image or frame of a video is recorded from two different viewing angles, such as the 3D stereoscopic parallax, and, when calibrated, can determine depth as is estimated from the measure of parallax error. Thus, the depth of a point on one sensor is inversely proportional to the distance between the secondary image of this point. So one can understand that individual pixels may be used or all the available pixels may be used to create the 3D virtual mapping. The mapping is called "virtual" or "augmented" because it only exists in the software as is then converted to images which may be overlayed over RR images or otherwise rendered.

Depth can also be calculated by introducing a triangulation method or a phase shift algorithm. In addition, a time-of-flight sensor can measure the time it takes light to travel from the system to each point of the object for higher accuracy. The present invention may use one or more of these technologies.

Alternatively, depth estimation may be calculated by the use of a single camera sensor through mono-camera depth estimation techniques.

The first feature of the VMGS system is that it is real-time, or within a few milliseconds of real-time, and one or more laparoscopic instruments with cameras in the body are needed to accomplish the mapping and guidance.

At the same time and in combination with the mapping set out above, one can may add the techniques of Simultaneous Localization and Mapping (SLAM) technologies to provide the system with enhanced spatial awareness of the cameras, instruments, tools, and organs n the body cavity in real-time using SLAM sensors and software technologies. SLAM means the process of determining the position and orientation of a sensor with respect to its surroundings, while simultaneously mapping the environment around that sensor. There are several types of SLAM sensors, which may be housed in the distal end of the laparoscopic instrument, including, but not limited to, acoustic sensors which use Time of Flight (ToF) techniques to measure or cross-check distance and location, laser rangefinders, and visual sensors.

Building the data maps is also possible with a single or double 3D vision camera, and unlike other forms of SLAM technology as long as there are a sufficient number of points being tracked through each frame, both the orientation of the sensor and the structures in the body cavity can be understood and represented in virtual format.

These sensors may be in the laparoscopic instrument, or in a specialized instrument that is like the laparoscopic instrument but contains only the SLAM sensors.

In addition, the environment around the sensor(s) however placed, may augmented to mapped as described above using either light detection and ranging (LIDAR), which may or may not be single pixel LIDAR. Each of these added technologies add another layer of accuracy and redundancy. These may be housed in the Scopetrx laparoscopic device or be on a separate instrument inserted into the body cavity.

At this point everything exists in software. Then, the next step is to use the localization information, such as real-time visual odometry from everything coming from external to internal in the body cavity and to localize all the laparoscopic instruments, tools, and other instruments to put them in their place inside the mapped area.

Then the real-time video information is augmented with the above mapped items and displayed in the AR/XR headset or on a 3D monitor or the 3D visualization method. Thus, when the surgeon is wearing the AR/XR headset he is able to see the outside of the patient in RR while at the same time "seeing" virtually inside the body cavity to understand from a visual representation the location and travel of the tools and things which inside outside the body cavity, as placed inside from the external through trocars or "ports". So, a surgeon can see the RR image of the patient surgery site, while at the same time seeing a virtual representation of all the structures and instruments inside the body cavity and see as they move. This real-time modeling a virtual imaging provides guidance to the surgeon on where his instruments are as well as where the structures of the body cavity and organs exist in relationship one to the others.

While the embodiment of this invention may create either with color or monochrome camera sensors, a monochrome sensor each pixel 8 bits, while in color sensors each pixel has 8 bit each for the red, green blue channels. Thus, slower frame rates will be the result of the above with color sensors. On the other hand, a monochrome sensor can achieve a higher resolution with faster processing and may be preferred.

Frame rate of the RR video is expressed in frames per second (FPS) which is the frequency rate at which consecutive images called frames appear on a display. Increasing the frame rate of video may divide this sequence of images into smaller periods of time, which is another method to reduce the latency and improve system performance, which is beneficial in a laparoscopic visualization situation.

In addition, this Virtual Mapping System provides the surgeon with collision avoidance mechanism, because the surgeon can see the virtual information, mapped in 3D, and correctly spaced, so that the surgeon does not puncture an organ in error or permit the tools inside to conflict on with another. In addition, the system, knowing where each instrument, tool and organ exist, as things move and are updated frame-by-frame in real-time, may be pre-programmed to identify and send alerts in the form of audio or visual cues in the virtual overlay of the RR video, so that when an instrument is getting too close to a pre-programed distance from an organ or other tool the alert will sound.

The surgeon, hospital, or manufacturer can set tolerances to be tight or loose, depending on the application and the surgery protocol.

The LED Lighting System

The LED lighting system serves several purposes. First, it provides internal light for the sensors to capture the environment. Second, some of the energy from the battery to the LED lights may be "bled" off before the laparoscopic instrument is inserted into the body cavity, permitting the glass or optical plastic housing surrounding the camera(s) and LED lights (and other sensors) to heat up to the temperature of the body cavity, and thus avoid "fogging" of the tool upon entry. Currently, fogging of laparoscopic camera tools is common and can waste up to 15 minutes of each surgery to correct. Third, to compensate for texture-less surfaces, like a stomach or gall bladder, LED lights in various wave-lengths, from ultraviolet and infrared LEDs can be used to project a specific pattern at the same time as lighting the area. By the introduction of structured light or structured illumination, as it is sometimes known, the light is projected known shading pattern which can assist the determination of the exact shape of a texture-less surface. The result is the projection of a known light pattern on the captured scene which can be un-sourced in processing. When applied to a texture-less surface the light patterns help make 3D imaging more realistic. The light patterns are created by lenslets on each of the LED's which create a specific pattern. The lenslets may also exist and be covering a "Hartmann-Shack" type wavefront sensor (SHWFS). When used with LEDs for structured lighting is beneficial because LEDs are intrinsically non-coherent, as opposed to lasers, the latter of which can create a "speckle effect", which is the actual scattering of coherent radiation. Thus, LED's provides the best option. Small lenslets are applied to the LEDs to create the structured light which is removed in post-processing of the image(s).

The main purpose of structured light projection is to detect and measure the deformation of the expected pattern of the organs in the body cavity. As an immediate consequence, structured light is used in 3D reconstruction of objects. to reconstruct texture-less surfaces, which are common in internal organs. The structured light is then removed, if desired, for viewing in the 3D AR/XR headset or 3D monitor.

It will be apparent to those skilled in the art that various modifications and variations can be made without departing from the spirit or scope of the disclosure. Since modifications, combinations, sub-combinations and variations of the disclosed embodiments incorporating the spirit and substance of the disclosure may occur to persons skilled in the art, the invention should be construed to include everything within the scope of the appended claims and their equivalents.

What is claimed is:

1. A laparoscopic imaging apparatus comprising:
   a handle subsystem;
   a shaft extending outwardly from the handle subsystem between a proximal end opposite a distal end, wherein a longitudinal axis extends through the shaft, between the proximal and distal ends;
   a trocar piercing tip coupled to the distal end of the shaft and movable between an open position and a closed position;
   a first laparoscopic tool positioned within the shaft and extendable through the trocar piercing tip, the first laparoscopic tool rotatable about a first axis parallel to the longitudinal axis and including a camera sensor mounted to a camera gimbal assembly configured to rotate the camera sensor about a second axis that is orthogonal to the first axis; and
   a second laparoscopic tool positioned within the shaft and extendable through the trocar piercing tip;
   wherein the handle subsystem includes a control handle configured for attachment and actuation of the first and second laparoscopic tools.

2. The laparoscopic imaging apparatus of claim 1, wherein the second laparoscopic tool includes a biopsy tool.

3. The laparoscopic imaging apparatus of claim 1, wherein the second laparoscopic tool includes an auxiliary illumination tool mounted to a second gimbal assembly.

4. The laparoscopic imaging apparatus of claim 1, wherein the second laparoscopic tool includes at least one of a insufflator, grasping forceps, bipolar forceps, scissors, biopsy spoon, needle driver, torcher, and cryosurgical tool.

5. The laparoscopic imaging apparatus of claim 1 further comprising a flexible sleeve covering the camera gimbal assembly allowing angular gimbal movement.

6. The laparoscopic imaging apparatus of claim 1, wherein the first laparoscopic tool includes an LED guide bar.

7. The laparoscopic imaging apparatus of claim 1, wherein the control handle includes a control roll wheel for rotating the first laparoscopic tool about the first axis and a safety trigger providing an interlock to prevent rotation of the control roll wheel.

8. The laparoscopic imaging apparatus of claim 1, wherein the control handle includes a wireless transceiver for transmitting images captured by the camera sensor.

9. The laparoscopic imaging apparatus of claim 1, wherein the control handle includes a rechargeable battery and an embedded battery.

10. A system for use in performing laparoscopic surgery comprising:
    an Augmented and Extended Reality (AR/XR) headset; and
    a laparoscopic imaging apparatus including:
    a control handle;
    a shaft extending outwardly from the control handle between a proximal end opposite a distal end, wherein a longitudinal axis extends through the shaft, between the proximal and distal ends;
    a trocar piercing tip coupled to the distal end of the shaft and movable between an open position and a closed position;
    a first laparoscopic tool positioned within the shaft and extendable through the trocar piercing tip, the first laparoscopic tool rotatable about a first axis parallel to the longitudinal axis and including a camera sensor mounted to a camera gimbal assembly configured to rotate the camera sensor about a second axis that is orthogonal to the first axis;
    a second laparoscopic tool positioned within the shaft and extendable through the trocar piercing tip; and
    a wireless transceiver for transmitting images captured by the camera sensor to the AR/XR headset;
    wherein the control handle is configured for attachment and actuation of the first and second laparoscopic tools.

11. The system of claim 10, wherein the second laparoscopic tool includes a biopsy tool.

12. The system of claim 10, wherein the second laparoscopic tool includes an auxiliary illumination tool mounted to a second gimbal assembly.

13. The system of claim 10, wherein the second laparoscopic tool includes at least one of an insufflator, grasping forceps, bipolar forceps, scissors, biopsy spoon, needle driver, torcher, and cryosurgical tool.

14. The system of claim 10, wherein the laparoscopic imaging apparatus includes a flexible sleeve covering the camera gimbal assembly allowing angular gimbal movement.

15. The system of claim 10, wherein the first laparoscopic tool includes an LED guide bar.

16. The system of claim 10, wherein the control handle includes a control roll wheel for rotating the first laparoscopic tool about the first axis and a safety trigger providing an interlock to prevent rotation of the control roll wheel.

17. The system of claim 10, wherein the control handle includes a rechargeable battery and an embedded battery.

18. The system of claim 10, further comprising an autostereoscopic monitor for displaying images captured by the camera sensor and received via the wireless transceiver.

* * * * *